United States Patent
Cole et al.

(10) Patent No.: US 7,155,868 B2
(45) Date of Patent: Jan. 2, 2007

(54) CAULKLESS PANELIZED WALL SYSTEM

(75) Inventors: Dawn R. Cole, Crestline, CA (US); Weiling Peng, Alta Loma, CA (US)

(73) Assignee: James Hardie International Finance B.V., Amsterdam (NL)

( * ) Notice: Subject to any disclaimer, the term of this patent is extended or adjusted under 35 U.S.C. 154(b) by 0 days.

(21) Appl. No.: 10/306,912

(22) Filed: Nov. 27, 2002

(65) Prior Publication Data

US 2003/0131550 A1   Jul. 17, 2003

Related U.S. Application Data

(60) Provisional application No. 60/333,967, filed on Nov. 28, 2001, provisional application No. 60/334,138, filed on Nov. 28, 2001, provisional application No. 60/334,144, filed on Nov. 28, 2001.

(51) Int. Cl.
*E04B 1/62* (2006.01)
(52) U.S. Cl. .............................. 52/394; 52/460; 52/469; 156/71; 156/574
(58) Field of Classification Search ............... 52/311.1, 52/314, 483.1, 315, 384, 344, 346, 745.09, 52/746.21, 460, 396.04, 395, 394, 469, 471
See application file for complete search history.

(56) References Cited

U.S. PATENT DOCUMENTS

| | | | | |
|---|---|---|---|---|
| 1,357,350 A | * | 11/1920 | Schumacher | 428/156 |
| 2,078,049 A | * | 4/1937 | Benedict | 52/417 |
| 3,109,206 A | * | 11/1963 | Beam | 52/417 |
| 3,881,292 A | * | 5/1975 | Porter | 52/461 |
| 3,977,465 A | | 8/1976 | Tank | |
| 3,984,269 A | * | 10/1976 | Schneller et al. | 156/71 |
| 4,071,984 A | * | 2/1978 | Larrow | 52/79.1 |
| 4,366,814 A | | 1/1983 | Riedel | |
| 4,450,022 A | | 5/1984 | Galer | |
| 4,452,831 A | | 6/1984 | Eichberger et al. | |
| 4,549,653 A | | 10/1985 | Lauritzen | |
| 4,612,075 A | | 9/1986 | Waugh et al. | |
| 4,802,315 A | | 2/1989 | Reed | |
| 4,837,070 A | | 6/1989 | Weber et al. | |
| 4,915,758 A | | 4/1990 | Baggett, Jr. et al. | 156/73.1 |
| 5,295,339 A | | 3/1994 | Manner | |
| 5,465,547 A | | 11/1995 | Jakel | |
| 5,487,250 A | * | 1/1996 | Yount et al. | 52/417 |
| 5,512,612 A | | 4/1996 | Brown et al. | |
| 5,547,743 A | | 8/1996 | Rumiesz, Jr. et al. | |
| 5,711,124 A | | 1/1998 | Stough et al. | |
| 5,732,520 A | * | 3/1998 | Maietta | 52/483.1 |

(Continued)

FOREIGN PATENT DOCUMENTS

DE   37 33 248 C1   2/1989

(Continued)

OTHER PUBLICATIONS

Patent Abstracts of Japan, Pub. No. 2000064465, Tsukasa.

(Continued)

*Primary Examiner*—Korie Chan
(74) *Attorney, Agent, or Firm*—Gardere Wynne Sewell LLP

(57) ABSTRACT

Disclosed herein are caulkless panelized wall systems and methods for their construction, wherein the wall systems have elastomeric joints that are resistant to cracking. Building panels are fastened to a frame with the edges adjacent to each other. No caulk is applied to the seam between the building panels. A backing material is applied over the seam between the panels and the wall is then finished with an elastomeric finish.

40 Claims, 30 Drawing Sheets

U.S. PATENT DOCUMENTS

| | | | |
|---|---|---|---|
| 5,857,730 | A | 1/1999 | Korpi et al. ............ 296/146.1 |
| 5,895,536 | A | 4/1999 | Starr et al. |
| 5,962,089 | A | 10/1999 | Jones et al. |
| 5,966,885 | A | 10/1999 | Chatelain |
| 6,179,201 | B1 | 1/2001 | Chess |
| 6,226,946 | B1* | 5/2001 | Stough et al. .............. 52/417 |
| 6,308,491 | B1* | 10/2001 | Porter ...................... 52/794.1 |
| 6,331,336 | B1 | 12/2001 | Szonn et al. |
| 6,491,468 | B1* | 12/2002 | Hagen ....................... 403/291 |
| 6,516,580 | B1 | 2/2003 | Maietta |
| 6,976,345 | B1* | 12/2005 | Keshmiri ................ 52/745.05 |
| 2001/0028943 | A1 | 10/2001 | Mashiko et al. |
| 2001/0034984 | A1* | 11/2001 | Murphy et al. ............ 52/204.5 |
| 2002/0146953 | A1* | 10/2002 | Lubker, II ................. 442/187 |
| 2003/0068457 | A1* | 4/2003 | McCain .................... 428/40.1 |
| 2003/0216097 | A1* | 11/2003 | Schmid ..................... 442/381 |

FOREIGN PATENT DOCUMENTS

| | | |
|---|---|---|
| DE | 297 18 716 U1 | 3/1998 |
| EP | 0673657 | 9/1995 |
| EP | 0683216 | 11/1995 |
| FR | 2 764 032 A1 | 12/1998 |
| GB | 2353249 | 2/2001 |
| TW | 88220820 | 10/1977 |
| TW | 77107188 | 12/1988 |

OTHER PUBLICATIONS

International Search Report.
International Preliminary Examination Report for Corresponding PCT/US 02/38121.

* cited by examiner

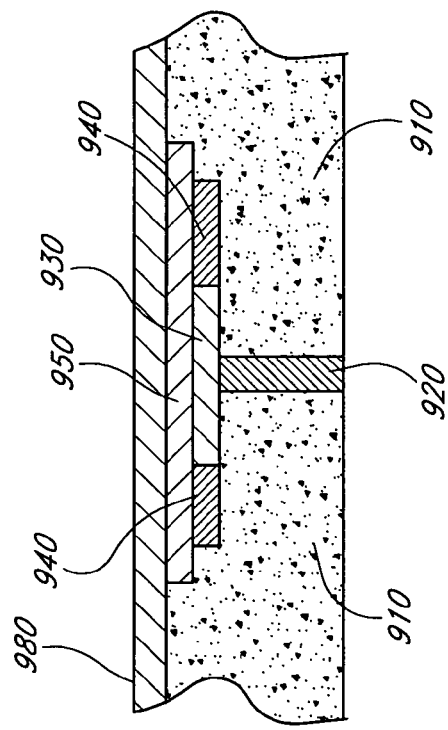
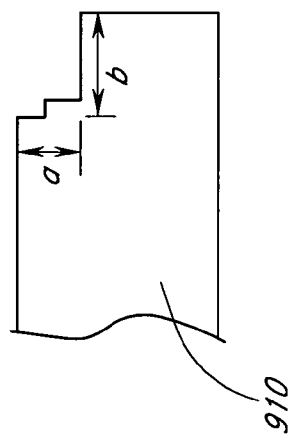
FIG. 12A
FIG. 12B

CAULKLESS PANELIZED WALL SYSTEM

RELATED APPLICATIONS

This application claims priority to U.S. Provisional Patent Application Ser. No. 60/333,967, filed Nov. 28, 2001, U.S. Provisional Patent Application Ser. No. 60/334,138, filed Nov. 28, 2001, and U.S. Provisional Patent Application Ser. No. 60/334,144, filed Nov. 28, 2001, the disclosures of which are incorporated by reference in their entireties.

BACKGROUND OF THE INVENTION

1. Field of the Invention

The present application relates generally to walls made with building panels, and more particularly, to caulkless panelized wall systems with joints that are resistant to cracking.

2. Description of the Related Art

Every building tradition in the history of mankind has produced stuccowork. Examples of stuccowork range from the Aztec architecture of ancient Mexico to the architecture of North Africa and Spain. In modern times, stuccowork has been popular in residential construction since the 1920s, especially in dry, warm climates like the U.S. Southwest. Because of the many ways in which it can be treated, stucco remains a popular exterior finish for many building types. Since stucco is applied as a paste, it can be textured and will conform to almost any shape resulting in a smooth, seamless wall of monolithic appearance and sound structural integrity.

In spite of its ongoing popularity, many builders resist using stucco as an exterior finish in framed construction because of the problems associated with applying stucco to exterior walls. Traditionally, a stucco coating is a thin paste composed of Portland cement, sand, lime, and water. Successive layers of stucco paste are applied to a metal or plastic mesh fastened to the exterior of the wall. Stucco supported on framed construction is normally ⅞" thick and is applied in three applications: the first or scratch coat, the second or brown coat, and the third, a finish, colored, texture coating. Since each layer of stucco paste must dry and harden before the next is applied, it takes several days to finish a traditional stucco wall.

While hundreds of thousands of new housing units are built every year, only a fraction of those units use stucco as an exterior finish. Stucco's susceptibility to moisture damage, for example, limits its use in wet climates. Likewise, stresses caused by transporting stucco-finished transportable buildings prevent its use in the lucrative manufactured housing market.

Another method of producing a textured or stucco look is a Direct-applied Exterior Finish System or DEFS. In DEFS, panels of a substrate material are fastened to the framing followed by a finish texture coating. The texture coating may be applied as a single coat or in multiple thin coats, and often uses either a joint or full-wrap alkali-resistant fiberglass mesh to reinforce the coating against cracking. DEFS can be installed and finished in a much shorter time than traditional stucco, enabling shorter construction times.

DEFS have not enjoyed a large share of the exterior market, however, because thin DEFS coatings, which are relatively brittle, are incompatible with the movements of wall panels. The substrate panels will invariably move with respect to each other from building settling, temperature variations, or moisture absorption. These movements can cause cracking of the finish at the panel joints. To prevent this cracking, the joints are often covered with tape or filled with caulk. In many installations, both tape and caulk are used. In DEFS stucco applications over fiber cement, an alkali-resistant fiberglass mesh tape, 2" to 12" wide, joins the two adjacent fiber cement panels that are the substrate over which the stucco is applied.

One problem with these types of joints is "joint read," a phenomenon in which the joint underlying the finish is visible. Joint read breaks the desired monolithic appearance of the finished wall. Joint read is a particular problem with fiber cement substrates because fiber-cement-panel faces absorb moisture from the finish coat faster than the taped joint. This differential moisture absorption makes the joint visible. In joints covered with tape, the step formed by the edge of the tape and the panel surface can often be seen, especially with low-angle illumination. Cracks arising from the loss of adhesion or slipping at the edges of the tape cause another type of joint read.

"Peaking" is another type of joint read and is caused by movement of the fiber cement panels. This movement causes the adhesive bond between the joint tape and the caulk joint to fail, causing the stucco to separate from the caulk. As a result, the stucco covering the joint floats higher or lower than the surrounding area, giving the appearance of a peak. Peaking also results from the caulk shrinking during curing, pulling the adhered joint tape below the surface of the stucco. Peaking disrupts the monolithic appearance of the wall and destroys the integrity of both the stucco and the substrate.

Another option is a thin joint sealing tape. These tapes, however, are often waterproof. Consequently, they do not absorb the stucco mix, resulting in poor adhesion between the stucco and the tape, which leads to surface deformation.

A more serious problem is cracking at the joints. Cracking not only disrupts the monolithic look of the finish, but also allows moisture to get behind the stucco and rot or corrode the wood or steel structural framing. Furthermore, these cracks are entry points for insects or fungi, which can damage the interior of the wall.

Consequently, DEFS are rarely used where there is wide daily temperature variation especially when coupled with a high rate of wet/dry cycling. DEFS are also seldom used in the fast-growing manufactured housing market because of the additional stress placed on walls during transport. Solving the joint read and stucco-cracking problems could significantly expand the market for DEFS stucco applications using fiber cement and other substrates. Not only could builders use fiber cement substrates and stucco in wetter climates, but also fiber cement substrates and stucco use could be expanded to new markets such as manufactured housing and modular buildings.

One strategy for preventing cracking of a DEFS coating at the panel joints is to construct joints from elastomeric materials. These elastomeric joints absorb the stress created by the differential panel movements. Such joints may be used with flexible, latex-based texture coatings, often called latex stucco or synthetic stucco. These finishes are able to move with the joint without cracking, which would greatly expand the market for DEFS applications.

The effectiveness of such joints may be evaluated in test walls consisting of several panels assembled on a frame, constructed with the joint-to-be-tested. The test wall is finished with a DEFS coating and subjected to a racking test. The racking test applies an in-plane shear force to the test wall, resulting in relative panel movement, until the DEFS coating cracks. The distance of maximum deflection at which the finish cracks is a measure of performance of the panel joints. For example, in order to pass the International Congress of Building Officials (ICBO) AC 59 "Acceptance Criteria for Direct-Applied Finishing Systems" (September 1992), a test wall constructed according to the method described in ASTM E-72 (98) subjected to a racking load that causes the wall to deflect 1", does not develop any visible joint cracks.

The polymeric adhesives used in joint tapes in DEFS tend to soften and lose holding power at 120° F., a temperature often achieved on the exterior vertical walls of a building exposed to full summer sun. Fiber cement building panels may become saturated with water in wet environments if installed improperly or if the finish layer fails. Many adhesives bond poorly to wet substrates. The performance of adhesives used in manufacturing joint tapes for DEFS applications may be evaluated using the "180° peel test," a well-known method of evaluating the adhesive strengths of tapes. The 180° peel test measures the force required to break the adhesion of a joint tape applied to two substrates held at a 180° angle.

U.S. Pat. No. 5,732,520 describes a method for forming a single-coat, synthetic-stucco-finished exterior wall. First, fiber cement wallboard panels are installed onto a building frame with the adjacent edges of the panels forming narrow gaps. Polyurethane caulk is applied to the gaps, and low-profile fabric-backed joint tape is applied over the adjacent edges of the panels to cover the gaps and the caulk. A high build flexible resinous latex emulsion in next applied directly over the panels and adhesive tape to form a synthetic stucco finish. The moisture absorption properties of the fabric from which the tape is manufactured matches that of the wall panels. A stucco-finished joint constructed according to this patent with 3"-wide joint tape slips and cracks at the edges when stretched 3–5 mm. The relative motion of adjacent 4'×8' cementitious boards under normal conditions is greater than 3–5 mm, however. While the joint tape described in U.S. Pat. No. 5,732,520 distributes the joint movement somewhat, the adhesive used in this tape is not sufficiently strong to prevent the edges of tape from slipping under stress. Consequently, the edges of the tape slip, cracking the stucco coating. A wider tape, for example, a 6"-wide tape, might better withstand the movement, but at an increased cost.

Cracking may be also prevented by applying additional layers of stucco or a joint compound over the tape before applying the final coat of stucco. This method, however, is expensive, time consuming, and requires skilled workers. Moreover, this technique often fails to produce satisfactory results. Another method of preventing cracks is increasing the thickness of the stucco build. This method is also expensive and time consuming, however.

SUMMARY OF THE INVENTION

The present disclosure provides panelized wall systems constructed with and without caulk and methods of their manufacture. The disclosed panelized wall systems have elastomeric joints that are resistant to cracking.

Accordingly, a one embodiment provides a method of constructing a panelized wall system, with at least the steps of: positioning at least two building panels over a frame, wherein each panel comprises a front surface, a back surface, and a plurality of edges, the back surfaces of the panels are positioned over the frame, and the two panels are positioned adjacent to each other, forming a seam between the adjacent panels; fastening the panels to the frame; and forming a caulkless elastomeric joint comprising a backing material adhered over the seam, wherein the backing material is adhered to the front surfaces of the adjacent panels without any caulk applied to the seam between the adjacent panels.

In a preferred embodiment, the panels are fiber cement.

In a preferred embodiment, the adjacent panels are positioned with no gap between them. In another preferred embodiment, the adjacent panels are positioned with a gap between them. Preferably, the gap is about ⅛" wide.

In a preferred embodiment, the backing material is a fabric. Preferably, the backing material is from about 0.0005" to about 0.04" thick. The fabric is preferably a non-woven polyester fabric or a polyamide mesh. Preferably, the backing material is about 3" wide.

In a preferred embodiment, the backing material is applied as a joint tape, wherein the joint tape comprises an adhesive preapplied to a face of the backing material.

In a preferred embodiment, the caulkless elastomeric joint further comprises a ceramic putty applied over the backing material. In another preferred embodiment, the caulkless elastomeric joint further comprises an elastomeric joint filler applies over the ceramic putty.

In an preferred embodiment, an elastomeric finish is applied to the panelized wall system. Preferably, the elastomeric finish comprises an elastomeric primer and an elastomeric texture layer, or is a texture coating.

In a preferred embodiment, the frame is a wood frame. In a preferred embodiment, the frame comprises shear panels. In a preferred embodiment, the frame comprises a moisture barrier. In a preferred embodiment, the frame comprises a water break.

Another embodiment provides a panelized wall system comprising: a frame; at least two building panels positioned over the frame, wherein each panel comprises a front surface, a back surface, and a plurality of edges, the back surfaces of the panels are positioned over the frame, the two panels are positioned adjacent to each other, forming a seam between the adjacent panels with no caulk applied to the seam, the panels are fastened to the frame, and no caulk is applied to the seam; and a caulkless elastomeric joint comprising a backing material adhered over the seam between the adjacent panels, wherein the backing material is adhered to the front surfaces of the adjacent panels without any caulk applied to the seam between the adjacent panels.

In a preferred embodiment, the panels are fiber cement.

In a preferred embodiment, the adjacent panels are positioned with no gap between them. In another preferred embodiment, the adjacent panels are positioned with a gap between them. Preferably, the gap is about ⅛" wide.

In a preferred embodiment, the backing material is a fabric. Preferably, the backing material is from about 0.0005" to about 0.04" thick. The fabric is preferably a non-woven polyester fabric or a polyamide mesh. Preferably, the backing material is about 3" wide.

In a preferred embodiment, the backing material is applied as a joint tape, wherein the joint tape comprises an adhesive preapplied to a face of the backing material.

In a preferred embodiment, the caulkless elastomeric joint further comprises a ceramic putty applied over the backing material. In another preferred embodiment, the caulkless elastomeric joint further comprises an elastomeric joint filler applied over the ceramic putty.

In an preferred embodiment, an elastomeric finish is applied to the panelized wall system. Preferably, the elastomeric finish comprises an elastomeric primer and an elastomeric texture layer, or is a texture coating.

In a preferred embodiment, the frame is a wood frame. In a preferred embodiment, the frame comprises shear panels.

In a preferred embodiment, the frame comprises a moisture barrier. In a preferred embodiment, the frame comprises a water break.

BRIEF DESCRIPTION OF THE DRAWINGS

FIG. 12A and FIG. 12B are cross sections of a fourth embodiment of a building panel with an embossed edge and an elastomeric joint using the panel.

DETAILED DESCRIPTION OF THE PREFERRED EMBODIMENTS

Figure 1:
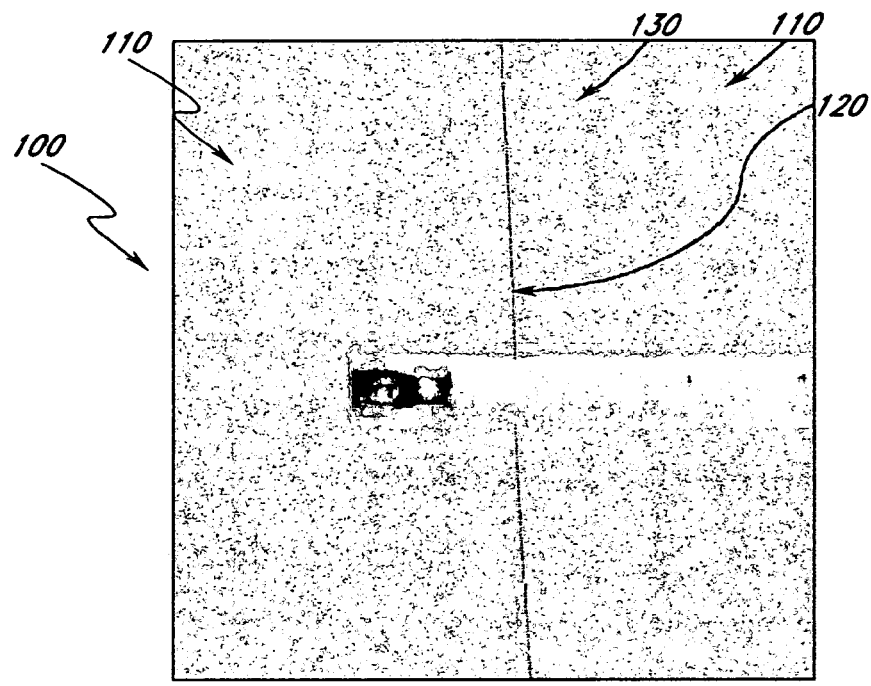
FIG. 1 is a photograph of a conventional fiber cement panel seam.

Disclosed herein is a system for constructing, from substrate panels, walls with synthetic stucco finishes that resist cracking. Embodiments of the disclosed wall system are constructed from combinations of the components defined below.

Definitions

Joint. The term "joint" as used herein refers both to a structure formed by the edges or corners of adjacent building panels, and a system of components used to fill or cover this structure. The intended meaning will be clear by context. The term "seam" is used interchangeably with the first sense of "joint," but not the second. A "joint" in the first sense or "seam is formed by two adjacent panels that have no gap between them, i.e., butted together, or with a gap between them.

Building Panels. The building panels of the present application are made from substrates suitable for interior or exterior construction. The panels may be flat or embossed, and may also have textured surfaces. The substrate may be inorganic, organic, or a combination thereof. Fiber reinforced inorganic substrates are preferred, for example glass mat reinforced cement boards, glass mat reinforced gypsum boards, and materials such as Georgia Pacific's Dens-glass Gold and United States Gypsum's Aquatough. It will be appreciated, however, that the method may be applicable to other fiber reinforced inorganic substrates as well as other substrates, including but not limited to aluminum, other cement composites such as scrimboard, wood, plywood, oriented strand board (OSB), wood composites, gypsum boards such as described in U.S. Pat. No. 5,718,759, the entirety of which is incorporated by reference, and plastics such as polymer foam composite panels such as expanded polystyrene foam.

A particularly preferred substrate is fiber cement (FC). Fiber cement panels can be fabricated by conventional methods, for example, the Hatschek process. Fiber cement panels can be either pretreated or untreated with a coating to modify water absorption through the panel face. Fiber cement panels can also be treated with a sealer, primer, or other coating.

While the components of the disclosed embodiments of the invention are selected to best work with fiber cement panels, it will be appreciated that similar components can be selected to achieve the same performance when used with building panels composed of other substrates.

Caulk. In those embodiments using caulk, the caulk is preferably a high solids, non-shrinking, permanently flexible caulk made from 100% polymer, such as a moisture cure polyurethane, moisture cure silicone-based adhesive, and silane-based adhesive. More preferably, the caulk is a 100%-solid moisture-cure polyurethane that has good adhesion to the cementitious boards, to the adhesive applied to the backing material, and to the backing material. An example of a suitable 100% polyurethane caulk such is Chem-calk 900 (Bostik Findley).

Adhesives. As described hereinafter, an adhesive layer is disposed between the building panel and a backing material. Elastomeric adhesives having long elongation are preferred adhesives. Preferably, the elongation is greater than about 20%. An adhesive layer preferably has a certain thickness that allows it to slip and distribute the movement of the panels to the entire backing material, preventing cracking of the finish coat. Thicker and softer adhesive layers generally slip more easily, although the minimum thickness required to provide the desired slip characteristics will vary for each different adhesive. A preferred adhesive layer thickness is from about 0.001" to about 0.04". A thinner adhesive layer is easier for the finish to hide, however, and may be preferred to provide a superior finish. The adhesive layer may include a single adhesive or several adhesives, for example, a dual adhesive system.

The elastomeric joints disclosed herein use an adhesive that is elastomeric, distributing the movement of the panels to the entire backing material. In certain embodiments, the adhesive also anchors the edges of the backing material to the building panel, preventing the edges from slipping. The adhesive may be a pressure-sensitive or non-pressure-sensitive adhesive. The former class of adhesives is particularly preferred. These adhesives are normally tacky at room temperature and adhere to a surface by application of light finger pressure. In another embodiment, a hot-melt adhesive is preferred.

The adhesive may include water-based, solvent-based, and 100% solid-based adhesives. Preferred adhesives include one-component and two-component adhesives. The adhesive may be based on, for example, general compositions of polyacrylate, polyvinyl ether, rubber (e.g., natural rubber), isoprene, polychloroprene, butyl rubber, neoprene rubber, ethylene propylene diene rubber (EPDM), polyisobutylene, butadiene-acrylonitrile polymer, thermoplastic elastomers, styrene-butadiene polymer, poly-alpha-olefin, amorphous polyolefin, silicone, ethylene-containing copolymer (e.g., ethylene vinyl acetate, ethylene ethyl acrylate, ethylene n-butyl acrylate, and ethylene methyl acrylate), polyurethane, polyamide, epoxy, polyvinylpyrrolidone and polyvinylpyrrolidone copolymers, polyesters, and mixtures or copolymers thereof. The adhesive layer may also contain additives or modifiers, for example, tackifiers, plasticizers, fillers, antioxidants, stabilizers, pigments, curatives, crosslinkers, solvents, etc.

Certain embodiments of the present invention further comprise a second adhesive. The second adhesive is relatively more rigid than the first adhesive. The rigid second adhesive, applied at the edges of the backing material, anchors the edges of backing material to the panels, preventing cracking of the finish at the edges of the backing material.

The second adhesive may be selected from the same class of adhesives as the first adhesive, i.e., pressure-sensitive or non-pressure-sensitive adhesives; hot-melt adhesives; water-based, solvent-based, and 100% solid-based adhesives; and one-component and two-component adhesives. Preferred second adhesives include, but are not limited to, water-based and solvent-based acrylic adhesives, modified acrylic adhesives, formaldehyde-based adhesives, moisture-cure polyurethanes, two-part polyurethanes, two-parts epoxies, one-part and two-part silicone-based adhesives, natural adhesives such as starch and protein, inorganic adhesives, polymer-latex adhesives, and mixtures thereof. In another preferred embodiment, the finish coat is the second adhesive. In this embodiment, the backing material is permeable to the finish coat, allowing the finish to adhere directly to the panel substrate beneath the backing material.

The first and second adhesives may be applied by solvent coating; extrusion, either separately from or simultaneously with the backing material; hot melt coating; calendaring; curtain coating; gravure or pattern coating; spray coating; lamination; pressure feed die coating; knife coating; roller coating; or any other suitable technique. It is expressly contemplated that the adhesive layers can be either continuous, such as a uniform layer, or discontinuous, such as strips or bands, dots, or another patterned or random arrangement of discrete adhesive portions. The thickness of adhesive is controlled according to the requirements of the application.

Preferred first and second adhesives include styrene-isoprene-styrene block-copolymer adhesives, for example PL919 pressure sensitive adhesive (SIA Adhesives); styrene-butadiene, polymer adhesives, for example H400 pressure sensitive adhesive (Heartland Adhesives & Coatings); and butyl rubber adhesives, for example PVT-3300 (Carlisle Coating & Waterproofing) and HL 2203 (H.B. Fuller). Another preferred second adhesive is a polyurethane adhesive, for example UR-0210 moisture-cured polyurethane (H.B. Fuller).

Backing Material. The backing material is a fabric or film to which the adhesive components of the disclosed panelized wall systems adhere, i.e., the adhesives, caulk, joint filler, ceramic putty, and finish coating, particularly cement-based stucco coatings and latex-based texture coatings. Preferably, the backing material stretches and moves with the building panels without tearing the backing material and without cracking the finish coating covering the backing material. Preferred backing materials include, but are not limited to, cellulose papers, plastic films, metal foils, and woven or non-woven fabrics.

Of these materials, fabric is preferred. Preferred fabrics are polyester, polypropylene, polyethylene, polyamide, cellulose, cotton, rayon, glass fiber, or combination of two or more of these materials. Preferably, the backing material has a selected moisture absorption characteristic that provides a monolithic appearance to the finish coat. The fabric should adhere well to the joint filler compounds and texture coatings of the disclosed panelized wall system. A preferred backing material is made from a non-woven polyester fabric, for example Sontara (Dupont). Sontara 8801 is 16 mil (0.016") thick, Sontara 8000 is 20 mil (0.020") thick, and Sontara 8004 is 25 mil (0.025") thick. Particularly preferred are backing materials made from a non-woven polyester fabric that is greater than about 16 mil thick. Another preferred backing material is made from a polyamide (Nylon) mesh fabric.

Preferred backing materials are easily bonded by the adhesives used herein, with good adhesion under dry, equilibrium, and water-soaked conditions, and at different temperatures. Preferably, the backing material has an elongation of about 20% or more, more preferably from about 20% to about 500%, wherein the preferred range includes elongations of about 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300%, 320%, 340%, 360%, 380%, 400%, 420%, 440%, 460%, 480%, and 500%.

A very thin fabric backing material may not be sufficiently strong to maintain a solid joint. On the other hand, a thick fabric may be difficult to hide beneath the finish. A preferred fabric thickness is from about 0.0005" to about 0.04", more preferably from about 0.001 " to about 0.03". A preferred width of backing material is from about ¼" to about 12". A more preferred width of backing material is from about ½" to about 8". A very narrow backing material may not sufficiently cover any gaps between the panels or effectively distribute the panel movements. A very wide backing material is less cost effective.

Joint Fillers. Certain embodiments of the disclosed elastomeric joint include one or more joint fillers applied over the backing material, adhesive layers, any troughs, and embossed edges or other edge profiling on the building panels. The joint filler fills any depressions in the joint or trough areas, providing a smooth surface for the texture coating. The joint filler preferably has elastomeric properties specifically selected to complement the expansion and contraction characteristics of the elastomeric tape applied beneath and finish coatings applied above the joint filler. The joint filler is preferably a mixture that includes a polymer binder, one or more inorganic fillers, thickeners, pigments, and inorganic binders.

Polymer latex emulsions such as acrylic emulsions are well known in the art and are suitable as the elastomeric polymer binder. Other suitable polymer binders include redispersable powdered acrylics, polyurethanes, and silicones.

Inorganic binders can be used in the joint filler material to provide hardness and scratch resistance. One example of a suitable inorganic binder is a combination of soda lime glass and acrylic acid, in which the soda lime glass reacts with the acrylic acid to form a gel. As this gel dries, it hardens the joint filler material.

Calcium carbonate, kaolin clay, aluminosilicate, and other silicate minerals are examples of suitable inorganic fillers, as are well known in the art. The inorganic filler may also be a low-density expanded mineral such as perlite. Hollow aluminosilicate or polymeric microspheres are examples of inorganic fillers that both modify the density of the joint filler and control the expansion and contraction characteristics.

Suitable thickeners are well known in the art, and include cellulose ethers, vegetable gums, clays, and synthetic polymers such as ammonium salts of acrylic polymers.

Pigments may be white, for example titanium dioxide, kaolin clay, or calcium carbonate, or colored, for example iron oxides. Pigments suitable for coloring the joint filler are well known in the art.

The joint filler may be smoothed over the joint by any method known to the art, for example by using a trowel and float. Typically, the joint filler is applied in one or more thin layers in order to minimize the visibility of the joint. As will become apparent below, the thickness of the joint filler application depends on a variety of factors including the thickness of the backing material, the thickness of the adhesive, the presence or absence of trough edges on the panels, and the presence or absence of other edge features on the panels. Once applied, the joint filler is typically allowed to cure (harden) for 1–4 hours, depending on temperature and humidity conditions. After curing, the joint filler may be smoothed by sanding. A preferred joint filler is a ceramic putty, for example Fill-n-Build (Global Coatings), which contains by weight acrylic copolymer emulsion (30%), hydrated aluminum silicate mineral (19.5%), soda lime borosilicate glass (10%), kaolin clay (8%), titanium dioxide (4%), and ammonium salt of acrylic polymer (1%).

Certain disclosed embodiments use an elastomeric joint filler, which provides an elastomeric surface to the exterior face of the joint. An elastomeric joint filler contains a higher proportion of polymer to make it more elastomeric, and is typically smoothed over the surface of the joint using a trowel and float and allowed to cure for about 1–4 hours, depending on temperature and humidity. A preferred elastomeric joint filler is Acracream (Global Coatings), which contains by weight acrylic polymer emulsion (55%), calcium carbonate (30%), polymeric microspheres (3.9%), and titanium dioxide (2%).

The elastomeric joint in certain embodiments of the present invention includes an elastomeric joint filler applied over a ceramic putty. Preferably, the elastomeric joint filler is selected to match the elastomeric properties of the synthetic stucco coating, further enhancing the crack resistance of the joint.

Finish. The finish is preferably an elastomeric finish and may be applied by any means suited to the particular finish, for example, troweling, spraying, rolling, or brushing. The finish coating is also referred to as "finish" and "surface coating."

A preferred finish is a textured finish simulating stucco, selected for its water resistance and flexibility. This type of finish is referred to as "synthetic stucco" or simply "stucco." Such finishes are well known in the art and are generally contain a polymer binder, inorganic filler, water, and pigments. Texture coatings are generally applied with a spray gun in one or more coats, for example, a primer and a texture layer, which are allowed to dry between coats. Commercially available synthetic stucco finishes compatible with the disclosed panelized wall systems include Multitex (Multicoat, Costa Mesa, Calif.), Akro-Gold (Omega Products), and Harditexture (James Hardie, Fontana, Calif.).

Suitable finish coats may also be applied by other means. For example, Colorseal Plus (Global Coatings) is applied to the entire wall using a paint roller and allowed to dry for 1 to 2 hours, providing a surface of uniform moisture absorption properties and uniform color. The composition of Colorseal Plus is typical and contains by weight aqueous acrylic emulsion (39%), calcium carbonate (35%), water (19%), titanium dioxide (5%).

A final coating of Carrara texture-coat is then shot onto the wall with a hopper gun. The surface may be left "as is" for a rough finish, or hand-troweled to the desired smoothness. The finish is protected until cured, typically 8–24 hours.

Frame. As used herein, a frame is any frame capable of supporting the disclosed panelized wall system. Preferred frames are wood or metal frames. Preferably, the vertical members of the frame are spaced about 16" apart, up to about 24" apart or more, and optionally wrapped in a moisture barrier.

Another preferred frame is a shear wall, a frame to which shear panels, typically plywood or oriented strandboard (OSB) panels, are attached for reinforcement. Other examples of a suitable frame include a tilt-up wall, or a previously finished wall, such as wall finished with a cladding.

Preferably, the building panels are positioned on the frame with the edges of adjacent panels sharing a common framing member, for example, a stud. In some embodiments, the panels are positioned with a gap of predetermined width between adjacent panels, the gap falling directly over a framing member. In another embodiment, the panels are installed without gaps, i.e., butted edge-to-edge. In embodiments with gaps between adjacent panels, the width of the gap is preferably from about 1/16" to about 1/8", allowing for building and panel movement, and shrinkage and expansion of the building panels. The bottom edges of the wall panels are preferably positioned on the wall level to ensure that the panels are level and plumb.

The building panels may be attached to the frame by any means known in the art. Mechanical means include nails, screws, staples, nuts and bolts, clips, and the like. The panels may also be fastened to the frame with chemical means, for example, with an adhesive or a tape. A predetermined pattern of fasteners is typically used to fasten the building panels to the frame. Preferred fasteners are screws and nails.

Moisture Barriers. Moisture barriers are used in certain embodiments of the disclosed panelized wall systems. Any type of moisture barrier, also called water barriers and weather-resistive barriers, known in the art may be used, for example asphalt paper, polyethylene-based sheeting, reinforced plastic sheeting, or foam insulation panels. A preferred moisture barrier is asphalt paper, also called asphalt-impregnated paper. The moisture barrier is installed between the frame and the building panels.

Water Management Systems. Certain embodiments of the disclosed panelized wall systems comprise water management systems, for example, water breaks, rain screens, or weep screens. Preferred water management systems are designed for use under panelized substrates, for example Homeslicker Rain Screen (Benjamin Obdyke, Horsham, Pa.). The water management system is typically installed beneath the building panels Release Liner. A release liner or release paper is a paper or plastic film coated with a release agent. The release liner is laminated to an adhesive layer, protecting the adhesive layer. A preferred release agent is a silicone-based polymer. The thickness of release liner is preferably from about 0.0002" to about 0.005". The release liner is easy to be peeled from the adhesive layer in order to expose the adhesive.

Testing. Tensile testing was performed on sample elastomeric joints made from 2"×5"⁵⁄₁₆" specimens of primed fiber-cement panel (Hardipanel, James Hardie, Fontana, Calif.) The sample joints were fabricated on the 2" sides of two panel specimens. In test samples with caulked joints, the caulk was a 100% polyurethane caulk (Chem-calk 900, Bostik Findley). The caulk was applied to a ⅛" gap between the panels, the caulk surface smoothed, and the caulk allowed to cure overnight. The test samples were finished with a medium texture (¹⁄₁₆") elastomeric latex stucco (MultiTex, Multicoat, Costa Mesa, Calif.). The thickness of the texture coating varied with the texture pattern, from about 0" to about ¹⁄₁₆".

Tensile testing was performed on a universal test machine (Instron). In the tensile tests, a sample test joint was mounted in the testing machine and stretched, typically at 6 mm/min, until the finish coating cracked. The strain of the joint at failure was calculated from the sample geometry and machine crosshead displacement.

Elastomeric Joints

FIG. 1 is a photograph of a conventional fiber cement panel joint 100. Panel joint 100 comprises two adjacent fiber cement substrate panels 110 separated by a ⅛" gap at the seam 120 and covered by tape 130.

Figure 2:
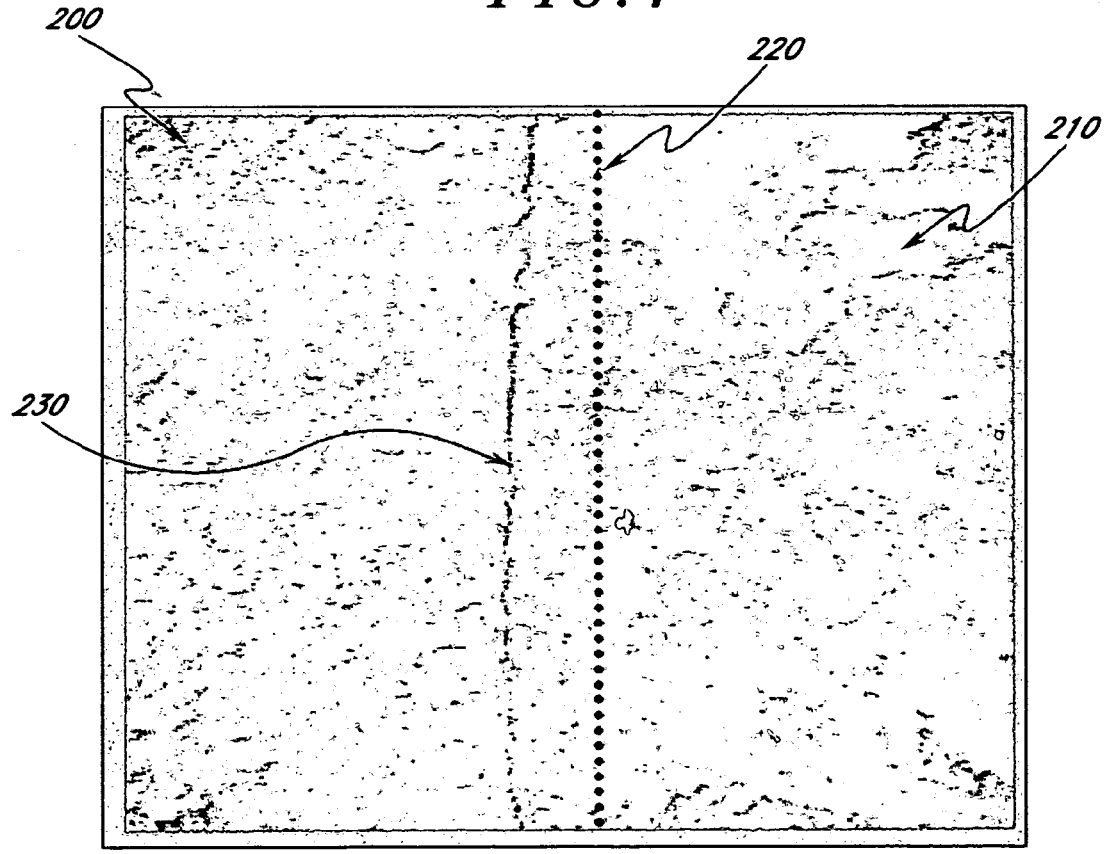
FIG. 2 is a photograph of an example of seam failure due to cracking on a conventional synthetic stucco application.

FIG. 2 is a photograph of a conventional synthetic stucco application 200. The stucco finish typically has a number of valleys 210. Valleys 210 are particularly susceptible to joint read, where cracks like crack 230 form near the joint 220. The cracks are caused by the movement between the fiber cement panels and the tape that joins two panels together beneath the stucco.

Figure 3:
FIG. 3 is a photograph illustrating "peaking" at a fiber cement panel seam.

FIG. 3 is a photograph of a synthetic stucco application where packing has occurred. Peaking is caused by movement of the fiber cement panels, more particularly, environmentally induced expansion and shrinkage. This movement causes failure of the adhesive bond between the substrate and the joint tape and caulk, causing the stucco over the joint to float higher or lower than the stucco over the field of the panels.

One embodiment of the present invention provides a building panel with a though adjacent to an edge of the panel. These trough-edge panels in conjunction with a joint tape create an elastomeric joint that is resistant to cracking at or near the joint and minimizes joint read caused by the height differential between the panel and the edge of the joint tape that covers the seam between adjacent panels. The panel is designed such that the edge of the joint tape lies in the trough, concealing the edges below the surface plane of the panel, such that the finish coat provides a uniform, flat finish.

Figure 4:
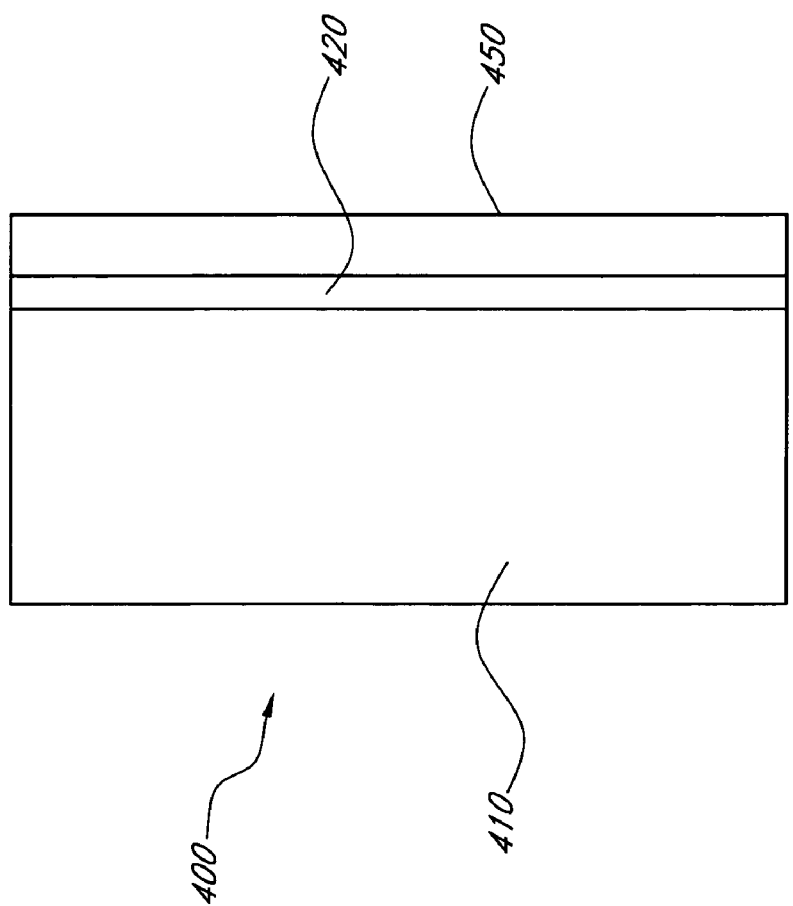
FIG. 4 is a top view of a trough-edge building panel.
Figure 5:
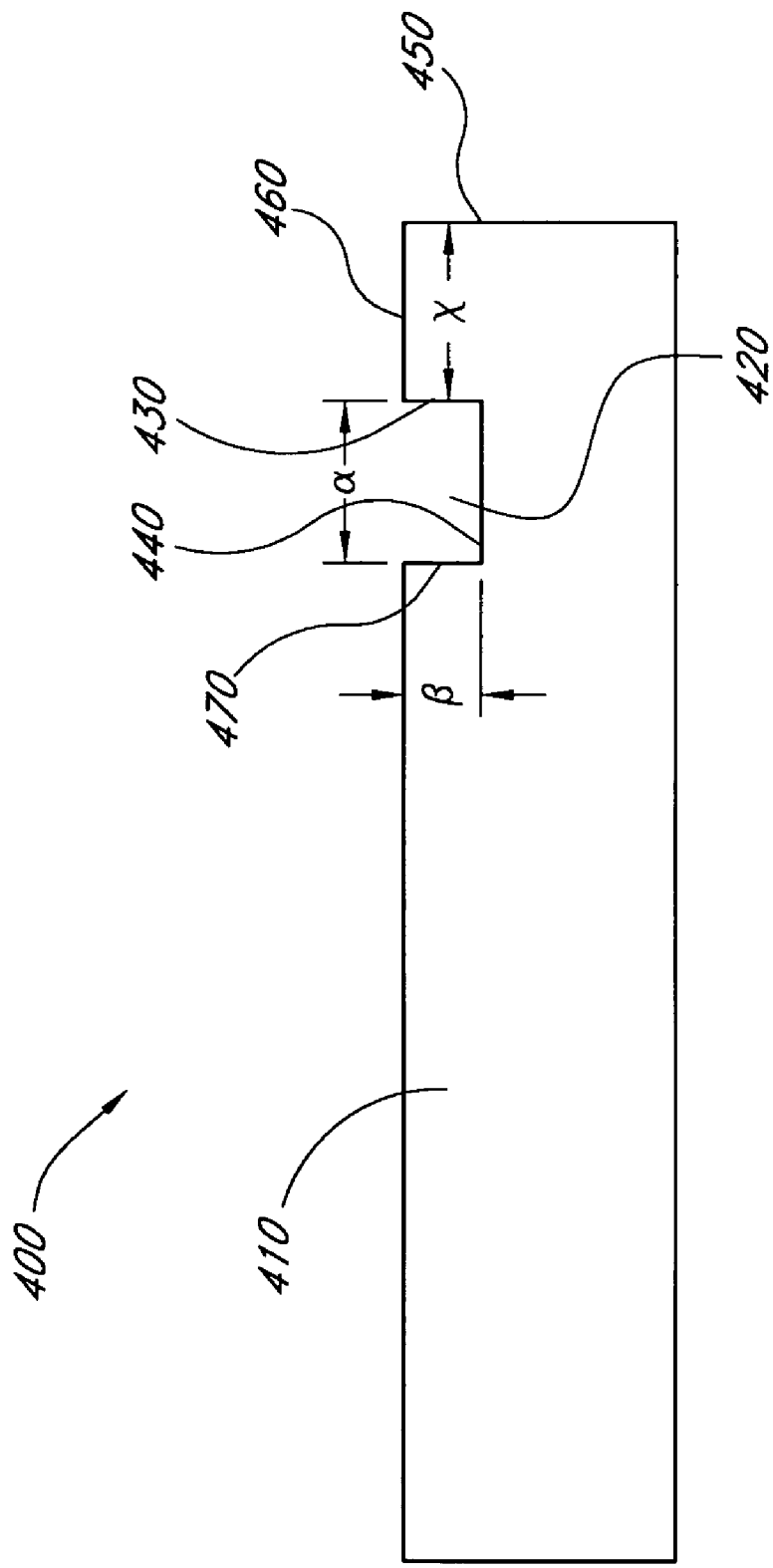
FIG. 5 is a cross section of a trough-edge building panel.
Figure 6:
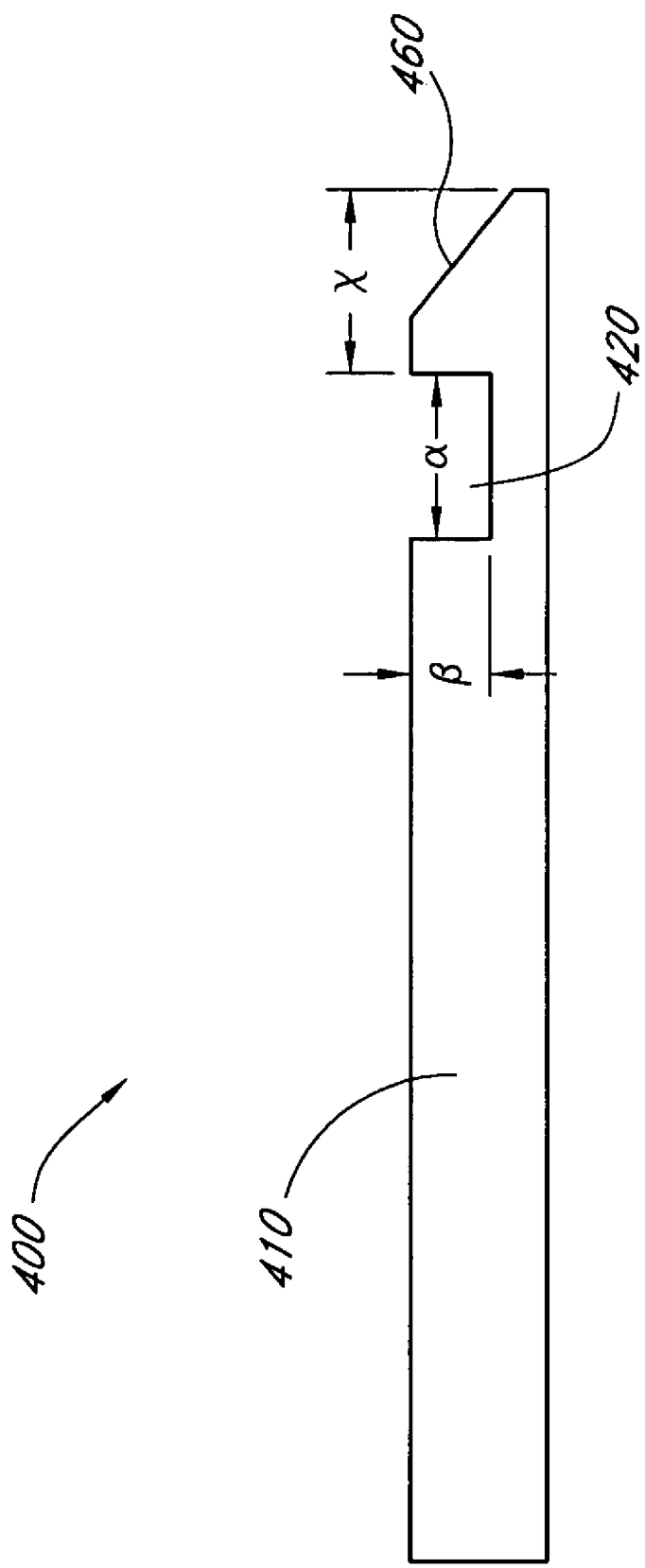
FIG. 6 is a cross section of an alternative embodiment of a trough-edge building panel.

FIG. 4 and FIG. 5 are top and cross sectional views, respectively, of a fiber cement panel 410 with a trough 420 according to one embodiment of the present invention, which overcomes the joint read and cracking problems illustrated in FIG. 2 and FIG. 3. The trough 420 is spaced inwardly from the edge 450 of the panel. In one embodiment, the side of the trough 420 closer to the edge 450 of the panel forms a wall 430, the wall meeting a floor 440 lower than the surface 460 of the panel between the trough 420 and the edge 450 of the panel. The embodiment illustrated in FIG. 5 also has a second wall 470 opposite to the first wall 430 that also meets the floor 440, forming a substantially rectangular trough 420. The edge of the joint tape preferably lies on the floor 440 of the trough 420. In a preferred embodiment, the trough 420 is spaced inwardly from the edge 450 of the panel by a distance χ of about 1 ". In this embodiment, the trough 420 has a rectangular cross section with a width α of about 0.63" and a depth β of about 0.034". In another preferred embodiment, the trough 420 extends to the edge of the panel such that trough 420 does not include a wall 430. FIG. 6 illustrates yet another embodiment in which the surface 460 between the trough 420 and the edge 450 of the panel slopes downwards towards the edge 450. The sloped surface reduces peaking in elastomeric joints that use caulk between the panels.

Fiber cement panel 410 may be fabricated by any method known in the art, for example, by the Hatschek process. The trough 420 may be formed by embossing, using a plate press, using a profiled accumulator roll in the Hatschek process, or by post-cure machining, as described below. The edges of the tape fall below the surface of the fiber cement panels 410, preventing joint read. The trough 420 illustrated in FIG. 5 and FIG. 6 has a rectangular cross section; however, it will be appreciated that the trough may assume other shapes, as described below.

Figure 7:
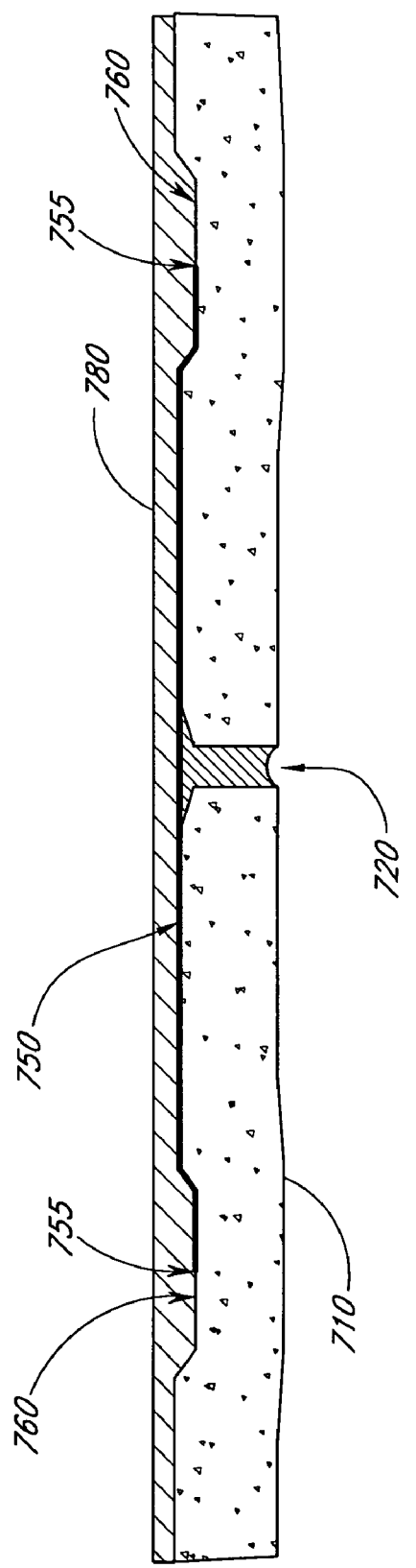
FIG. 7 is a cross section of an elastomeric joint formed at the seam of adjacent trough-edge panels.

FIG. 7 illustrates a joint incorporating a trough-edge panel. This system includes two adjacent panels 710 separated by a gap. In the illustrated embodiment, caulk 720 is applied to the gap. It will be appreciated that the gap and/or caulk are optional. For example, adjacent panels may be separated by a gap that is not caulked. A preferred embodiment described below, has neither a gap nor any caulk between adjacent panels. Tape 750 is applied over the edges of the panels 710, with the edges 755 of the tape falling inside the troughs 760 of the panels 710. Synthetic stucco 780 is applied over the panels 710 to cover the tape 750.

Figure 8:
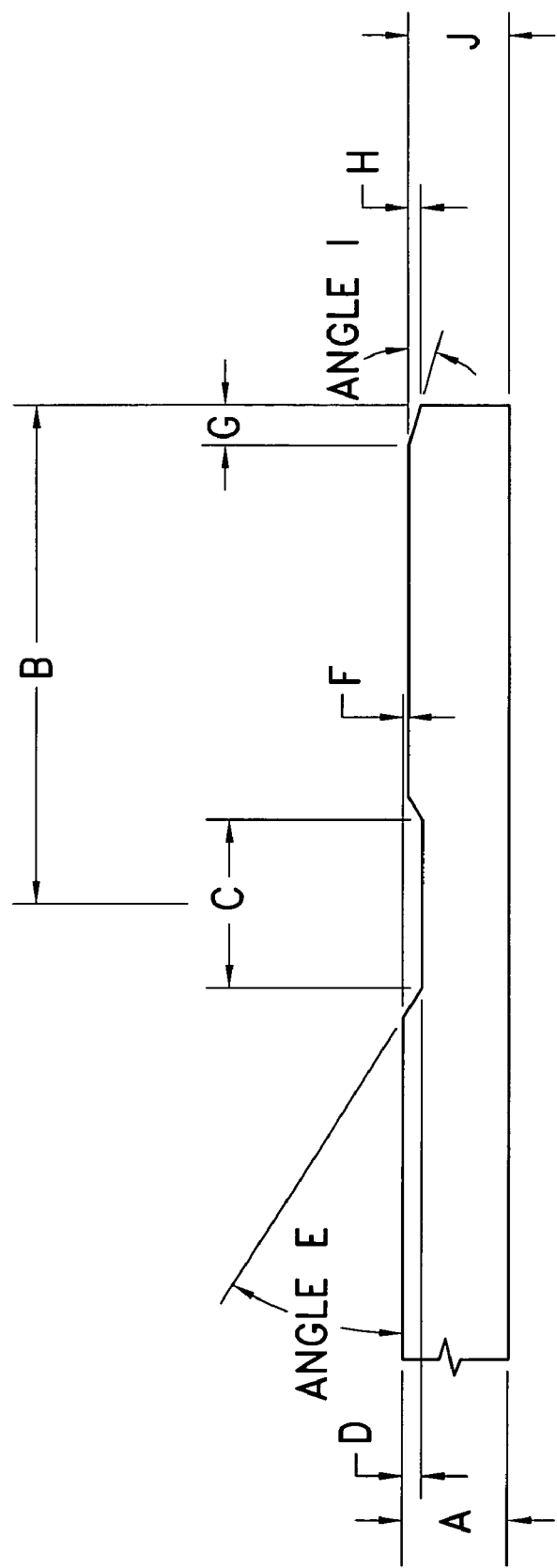
FIG. 8 is a key for the dimensions in TABLE 1 for a trough-edge building panel.

FIG. 8 is keyed to the dimensions of a preferred panel substrate provided in TABLE 1 below.

TABLE 1

| Feature | Reference | Preferred Range | Preferred |
|---|---|---|---|
| Board Thickness | A | about 3/16"–2" | about 5/16" |
| Trough Edge Offset | B | about 1/2"–3" | about 1 1/2" |
| Trough Width | C | about 1/8"–2" | about 3/4" |
| Trough Depth | D | about 0.005"–0.25" | about 0.050" |
| Trough Relief Angle | ∠E | about 5°–90° | about 45° or rounded |
| Surface Offset Depth | F | about 0–0.1" | about 0.010" |
| Edge Taper Width | G | about 0–0.25" | about 0.060" |
| Edge Taper Depth | H | about 0–0.25" | about 0.060" |
| Edge Taper Angle | ∠I | about 0–90° | about 15° |
| Edge Thickness | J | about 3/16"–2" | about 5/16" |

TABLE 1 provides preferred dimensions for fiber cement building panels. The board thickness A is selected for the particular building application. Thicker panels are stronger, but are heavier and more difficult to handle, more expensive, and require more warehousing space. The trough edge offset B and trough width C are selected such that the edges of the selected joint tape fall within the troughs of adjacent panels. Widening the trough width C allows for a greater range of joint tape widths to be used with a particular panel, as well as flexibility in providing a gap or no gap between adjacent panels. Without being bound by any theory, our current belief is that the motion of the panels is accommodated by that part of the tape outside the troughs, however. Accordingly, a narrower trough width C would provide a more flexible joint. Moreover, a narrow trough requires less joint filler or surface finish to fill, facilitating hiding the joint. The preferred dimensions for the trough edge offset and trough width contemplate a 3"-wide joint tape and either no gap or a gap no wider than about 1/8" between adjacent panels. The trough depth D is selected such that the top of the joint tape within the trough is approximately level with the board thickness A. Consequently, the preferred trough depth approximates the thickness of the joint tape. A trough relief angle E less than 90° makes hiding the joint easier. A shallower angle or rounded edge minimizes the visibility of the trough wall. The surface offset depth F reduces the panel thickness A to the edge thickness J, further reducing the changes in elevation in the taped joint, and again, reducing the visibility of the joint. The edge panel width G, depth H, and angle I are selected to reduce peaking in caulked joints. It will be appreciated that the features and dimensions illustrated in TABLE 1 are merely exemplifying, and thus, the panel can have other features and dimensions. For example, the very edge of the board can be cut with multiple angles, which may assist in eliminating peaking and/or the need for caulk.

EXAMPLE 1

Comparative Testing of Joint Flexibility for Trough-Edge Panels

Tensile testing of the flexibilities of joints constructed from panels with different embossed trough depths was performed on a universal testing machine at a strain rate of about 5 to 10 mm per minute. Three different joint configurations were tested on a substrate of 5/16"-thick fiber-cement panel (Hardipanel, James Hardie, Fontana, Calif.). Each joint was caulked, taped with 3"-wide tape, and finished with a synthetic stucco finish. The joints were caulked with a 100% urethane caulk (Chem-calk, Bostik Findley), taped with a 3"-wide elastomeric tape (Multicoat Elastomeric Joint Tape, Multicoat, Costa Mesa, Calif.) centered over the joint, and finished with a medium grit worm finish synthetic stucco (MultiTex, Multicoat, Costa Mesa, Calif.). In the panels with troughs, the troughs were spaced such that the edges of the tape fell within the troughs.

The testing results reported in TABLE 2 demonstrate the improved joint flexibility provided by joints made with trough-edge panels compared to those made with flat panels. The trough depths were selected to provide joint flexibility while maintaining an aesthetically acceptable appearance. In test A, the control, the panels were smooth with no edge trough. In test F, each panel was embossed with a single shallow batten with a rectangular cross section approximately 0.077" deep running the length of the panel. In test E, each panel was embossed with a single deep batten with a rectangular cross section approximately 0.086" deep running the length of the panel. In both trough-edge panels, the troughs edge offset (B) was 1 1/2" and the trough width (C) was 3/4".

As shown in TABLE 2, the panel with the shallow trough (test F) provided the most flexible joint system, stretching 10.48 mm (13.8%) before failing. In each case, the joint failed when the edge of the tape slipped from the panel surface at the top and bottom of the tape. In no case did the joint fail at the seam between the panels.

TABLE 2

| Test | Trough Depth | Tensile Joint Stretch to Failure |
|---|---|---|
| A | No Trough | 4.58 mm (6.0%) |
| F | 0.077" | 10.48 mm (13.8%) |
| E | 0.086" | 9.01 mm (11.8%) |

The results provided in TABLE 2 demonstrate that the joint flexibility as determined by joint stretch, more than doubled in the trough-edge joint F compared to the smooth, flat panel joint A. This greater flexibility translates into increased resistance to joint cracking. The added stucco finish used to conceal the trough also conceals the edges of the tape, reducing joint read. The trough-edge joint also demonstrated improved shear strength of the DEFS coating.

Irrespective of the thinness of a joint tape or backing material, when used on a flat panel, there will be a height difference between the top of the joint tape or backing material and the surface of the panel. FIG. 9–FIG. 12 illustrate panels with embossed edges designed to provide an improved finish. Preferably, the depth "a" of the embossed edge is the same as the thickness of the backing material and adhesives. Preferably, twice the width "b" of the embossed edge plus the width of any gap between adjacent panels equals the width of the backing material. The top surface of the backing material and the front surface of the panels are preferably coplanar, resulting in a monolithic appearance even when using a thin finish coat.

Figure 9A:
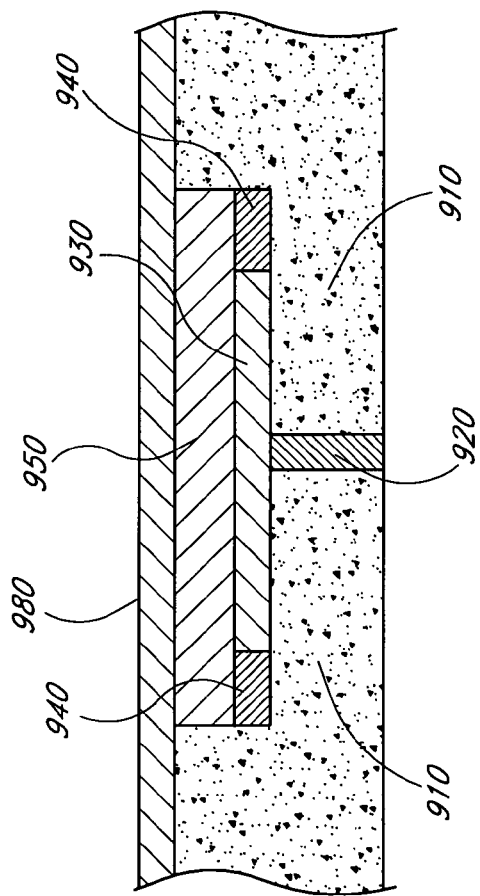
FIG. 9A and FIG. 9B are cross sections of a first embodiment of a building panel with an embossed edge and an elastomeric joint using the panel.
Figure 9B:
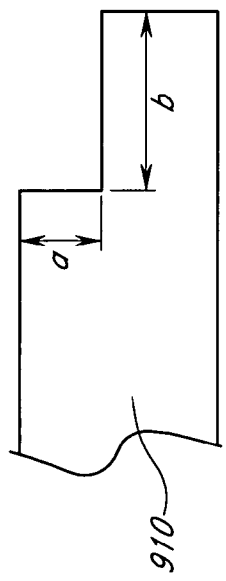
Figure 10A:
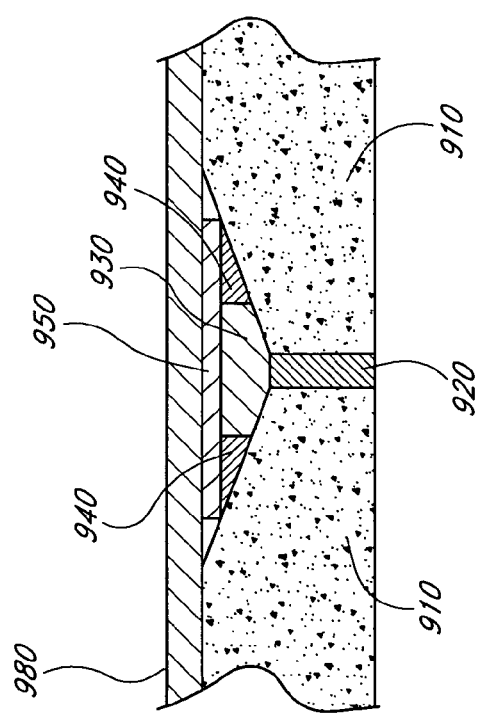
FIG. 10A and FIG. 10B are cross sections of a second embodiment of a building panel with an embossed edge and an elastomeric joint using the panel.
Figure 10B:
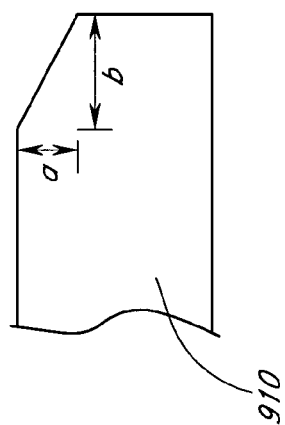
Figure 11A:
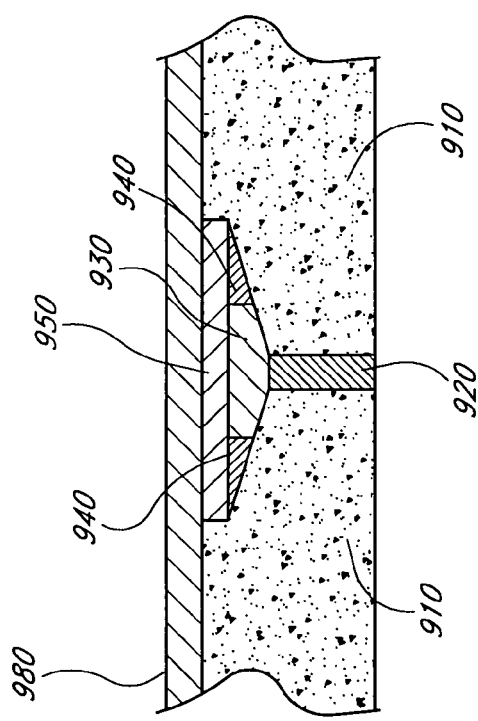
FIG. 11A and FIG. 11B are cross sections of a third embodiment of a building panel with an embossed edge and an elastomeric joint using the panel.
Figure 11B:
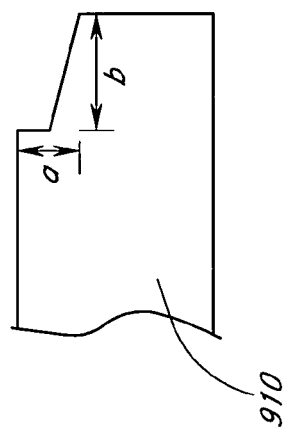

The embossed edge may be flat as in FIG. 9. It may be sloped as in FIG. 10 and FIG. 11, or have steps as in FIG. 12, or have curved profile (not shown), or any combination thereof. The transition between the side-wall and bottom of the embossed edge may be a sharp angle as in FIG. 9–FIG. 12 or curved (not shown). Panels with embossed edges may also comprise edge troughs as described above. The disclosed methods of fabricating elastomeric joints are applicable to flat panels, panels with embossed edges, trough-edge panels, and trough-edge panels with embossed edges.

For fiber cement panels, the embossed edges are preferably produced by embossing, although they may also be produced by other methods, for example by using a plate press, using a profiled accumulator roll in the Hatschek process, or by post-cure machining.

Figure 13:
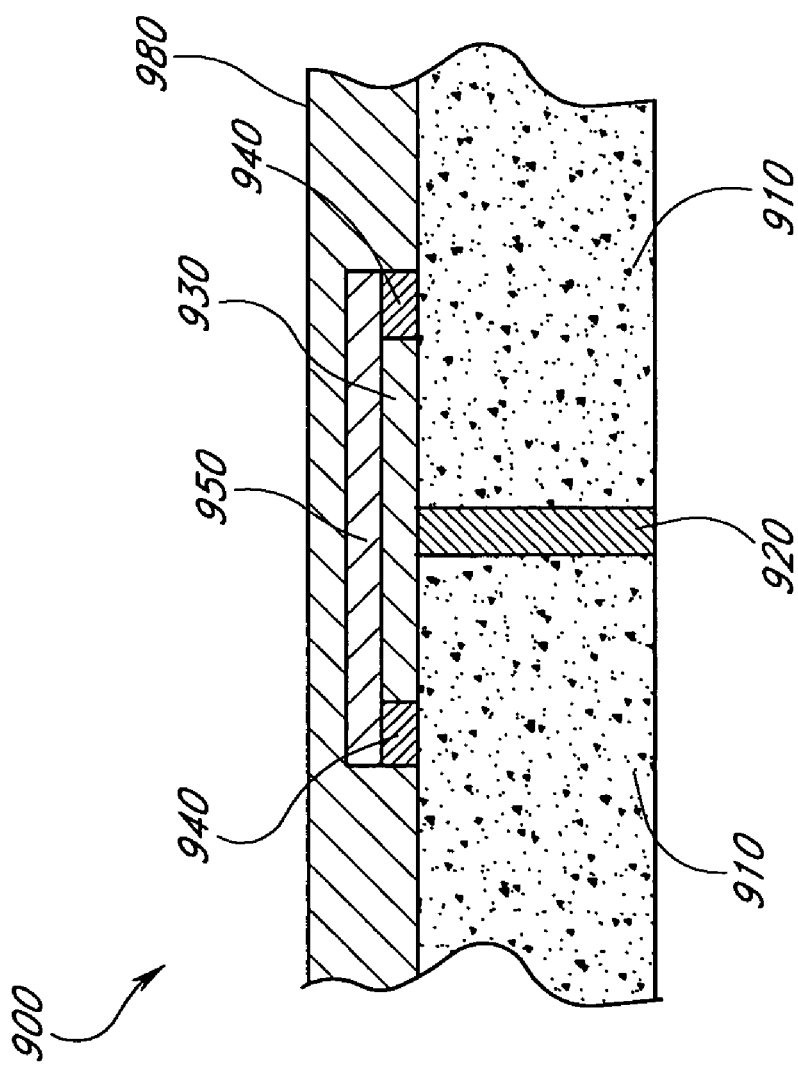
FIG. 13 is a cross section of a first embodiment of an elastomeric joint made according to METHOD 1–METHOD 10.
Figure 14:
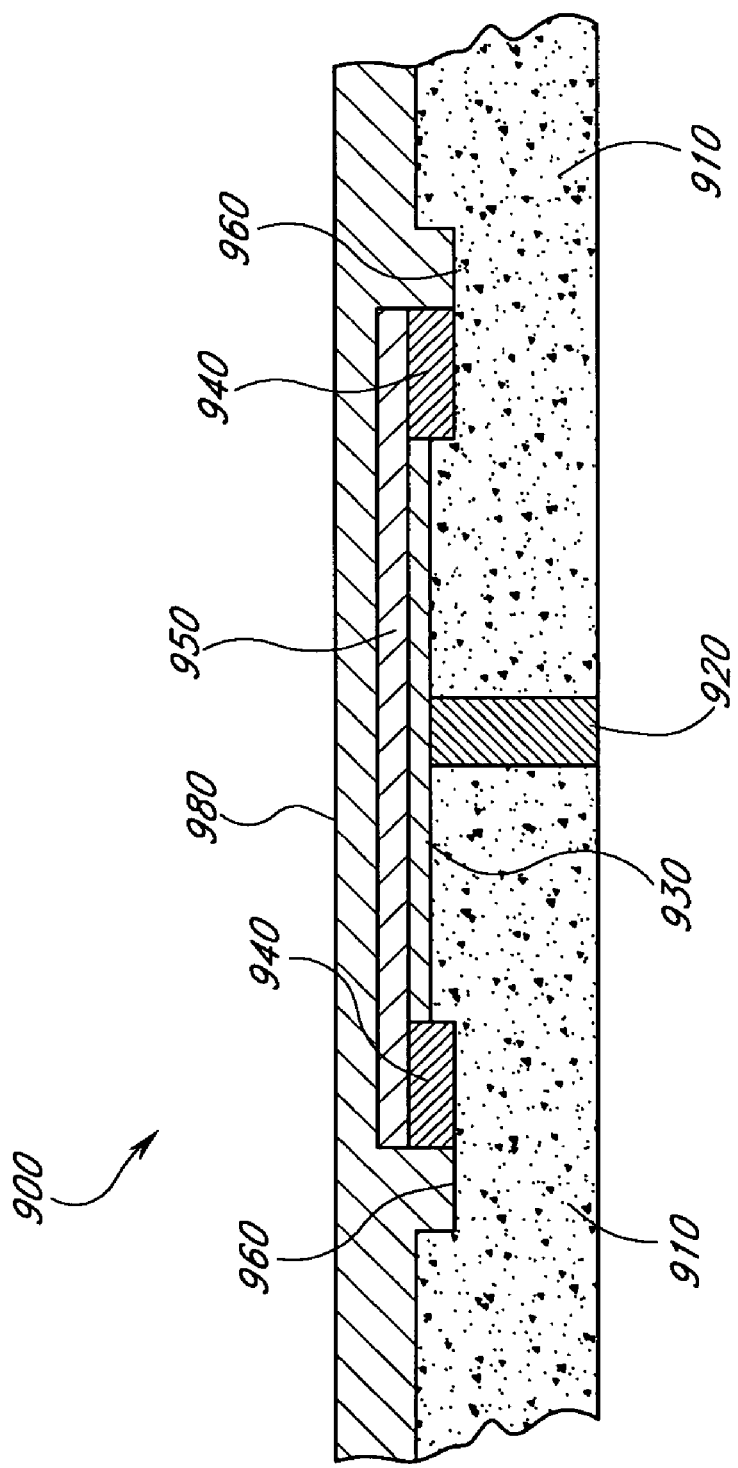
FIG. 14 is a cross section of a second embodiment of an elastomeric joint made according to METHOD 1–METHOD 10.

FIG. 13 and FIG. 14 are cross-sectional views of elastomeric joints 900 that include two adjacent panels 910; optionally, a caulk 920; a first adhesive 930; a second adhesive 940; a backing material 950. Certain embodiments of the elastomeric joint may also have a joint filler, as is discussed in greater detail below. The panels may be flat, as shown in FIG. 13; have trough edges 960, as shown in FIG. 14; have embossed edges (not shown); or a combination thereof. The surface is covered with an elastomeric finish 980, preferably, a texture coating or synthetic stucco finish. Adhesive 930 is at the center of the joint and adhesive 940 is at the edges of the joint. The adhesives and backing material distribute the panel movement from the seam formed by the panels to the entire backing material greatly reducing strain on the finish coating, which prevents cracking of the finish.

The caulk 920 fills the gap between adjacent panels 910. It provides a surface for the elastomeric adhesive or adhesives applied thereover, supporting the adhesives, backing material, and texture coating under tensile and compressive forces across the joint. A joint without caulk may show peaking at the joint or cracking in the coating.

The adhesive layer may include a single adhesive or dual adhesives. FIG. 13 and FIG. 14 illustrate a dual adhesive system. In a single adhesive system, adhesives 930 and 940 are the same adhesive. In a dual adhesive system two different adhesives are used. As shown in FIG. 13 and FIG. 14, a first adhesive 930 used in the central part of the joint is relatively more flexible than a second adhesive 940 used at the edges of the joint. The more flexible first adhesive 930 distributes the panel movements across the entire backing material 950, while the more rigid second adhesive 940 anchors the edges of the backing material, preventing cracks that arise from tape slippage.

EXAMPLE 2 and EXAMPLE 3 below illustrate the advantages of using both an adhesive layer and a backing material in an elastomeric joint. In EXAMPLE 2, the joint is fabricated without an adhesive layer. In EXAMPLE 3, the joint has no backing material. Neither joint successfully withstood significant panel movement.

EXAMPLE 2

Joint Without an Adhesive Layer

Two 2"×5" primed fiber cement specimens (James Hardie, Fontana, Calif.) were arranged with a ⅛" gap between them. The gap was filled with 100% polyurethane caulk (Chemcalk 900, Bostik Findley), the caulk surface smoothed, and the caulk allowed to cure overnight. A 2"×3" piece of backing material (Sontara 8801 fabric, Dupont) was centered and applied over the joint, and the surface finished with a medium texture (¹⁄₁₆") elastomeric latex stucco (Multicoat, Costa Mesa, Calif.). The thickness of the texture coating was from about 0" to about ¹⁄₁₆", varying with the texture pattern on the surface. No additional adhesive layer was applied between the cementitious board and the fabric. Instead, the texture coating penetrated the backing material reaching the fiber cement panel beneath, and adhering the backing material to the panels.

The sample was equilibrated at 72° F. at 50% relative humidity for 7 days before tensile testing. The texture coating cracked when the joint was stretched about 1.6 mm (2.1%) at about 6 mm/min at 72° F. Thus, this type of joint would not withstand the normal expected movement of 4'×8' fiber cement panels, which may shrink 3–5 mm or more (3.9–6.6% for a 3"-wide tape).

Other fabrics, such as other Sontara Series 8000 polyester fabrics (Dupont) and nylon fabrics were also tested in this type of joint. None withstood more than 3 mm (3.9%) of stretching before cracking the latex-based texture coating.

EXAMPLE 3

Joint without a Backing Material

Two 2"×5" primed fiber cement specimens (James Hardie, Fontana, Calif.) were arranged with a ⅛" gap between them. The gap was caulked and cured as described in EXAMPLE 2. A 2"×3" layer of 0.028" thick PVT-3300 adhesive (Carlisle Coating & Waterproofing Inc.) was centered and applied over the joint. The test sample was finished and the finish cured as in EXAMPLE 2. Tensile testing indicated that the texture coating cracked when the joint was stretched about 1–2.5 mm (1.3%–3.3%) at 6 mm/min at 72° F. Thus, this type of joint would not withstand the normal expected movement of 4'×8' fiber cement panels. Furthermore, because the adhesive layer did not absorb the latex-based texture coating, the joint was clearly visible after the coating cured.

EXAMPLE 4

Comparative Test of Backing Materials

A comparative test of backing materials was performed. The backing materials were three non-woven polyester fabrics (Sontara 8000, Sontara 8004, Sontara 8801, Dupont). For each test, a joint tape was prepared from a 2"×3" piece of the test backing material and a 0.006" layer of a styrene-isoprene-styrene block copolymer adhesive (PL 919, SIA Adhesives). For each test, the edges of two 2"×5" specimens of primed fiber cement panels were butted with no gap between them. The joint tape was centered on the joint and applied. The test sample was finished and the finish cured as described in EXAMPLE 2.

The test samples were equilibrated for 7 days at 72° F. at 50% relative humidity. Tensile testing was performed at 6 mm/min at 72° F., and the strain (stretching) at which the finish cracked was recorded. The properties of the backing materials and test results are provided in TABLE 3.

TABLE 3

| Backing Material | Elongation | | Stretch Before Cracking |
|---|---|---|---|
| | Machine Direction | Cross Direction | |
| Sontara 8000 | 38% | 114% | 10–12 mm (13.1–15.7%) |
| Sontara 8004 | 33% | 110% | 9–11 mm (11.8–14.4%) |
| Sontara 8801 | 18% | 78% | 4–7 mm (5.2–9.2%) |

This example shows importance of the elongation of the backing material to the performance of the joint. Because a joint movement of 3–5 mm is typical for 4'×8' panels, the 18% elongation of the Sontara 8801 fabric appears to produce an insufficiently flexible joint using a 3"-wide tape. Accordingly, we prefer a backing material with an elongation of about 20% or more.

The methods described below are the preferred methods of joining building panels with elastomeric joints. These methods preferably comprise some or all of following steps: applying caulk between adjacent building panels; applying adhesive on a backing material or on the edges of construction panels such as fiber cement panels; applying a release liner on the adhesive applied to the backing material or the edges of the panels; removing the release liner and applying an adhesive-coated backing material to adjacent fiber cement panels or applying a backing material to adjacent adhesive-coated fiber cement panels.

In practicing these methods, either a single adhesive or dual adhesives may be used as the adhesives 930 and 940 of FIG. 13 and FIG. 14. In a single adhesive system, adhesives 930 and 940 are the same adhesive. In a dual adhesives system, adhesives 930 and 940 are different adhesives. Preferably, the adhesive 930 is at the central portion of the joint and adhesive 940 is symmetrically disposed at the edges of the backing material. Adhesive 930 may contact adhesive 940, and in fact, may overlap adhesive 940. In another embodiment, adhesive 930 and adhesive 940 do not contact. The thicknesses of the layers of adhesives 930 and 940 may be the same or different.

Eleven methods of fabricating an elastomeric joint are described below. The preferred backing material may be the same or different for each method, and the preferred adhesive(s) may be the same or different in each method. The building panels for each method may have plain edges, trough edges, embossed edges, or a combination thereof. TABLE 4 below provides a brief summary of the first ten methods.

TABLE 4

| | Adhesive 930 | | Adhesive 940 | |
|---|---|---|---|---|
| Method | Location | When Applied [a] | Location | When Applied [a] |
| Single Adhesive Systems | | | | |
| 1 | Backing material | Before | N/A | N/A |
| 2 | Edge of panel | Before | N/A | N/A |
| 3 | Backing material or edge of panel | After | N/A | N/A |
| Dual Adhesive Systems | | | | |
| 4 | Backing material | Before | Backing material | Before |
| 5 | Backing material | Before | Backing material or edge of panel | After |
| | Backing material or edge of panel | After | Backing material | Before |
| 6 | Backing material or edge of panel | Before | Finish coat is adhesive 140 | After |
| 7 | Edge of panel | Before | Edge of panel | Before |
| 8 | Edge of panel | Before | Backing material or edge of panel | After |
| | Backing material or edge of panel | After | Edge of panel | Before |
| 9 | Backing material or edge of panel | After | Backing material or edge of panel | After |
| 10 | Backing material | Before | Edge of panel | Before |
| | Edge of panel | Before | Backing material | Before |

[a] "Before" means that the adhesive is installed prior to the installation of the building panels to the frame. "After" means that the adhesive is applied after the installation of the building panels to the frame.

An elastomeric joint for fiber cement panels may be made from a single adhesive plus a backing material. The adhesive is preferably an elastomeric material that slips with the movement of the building panels at the center of the joint, but does not slip at the edges of the backing material. The expected movements of 4'×8' fiber cement panels will not crack a flexible texture coating used with this joint system.

Method 1

Figure 15:
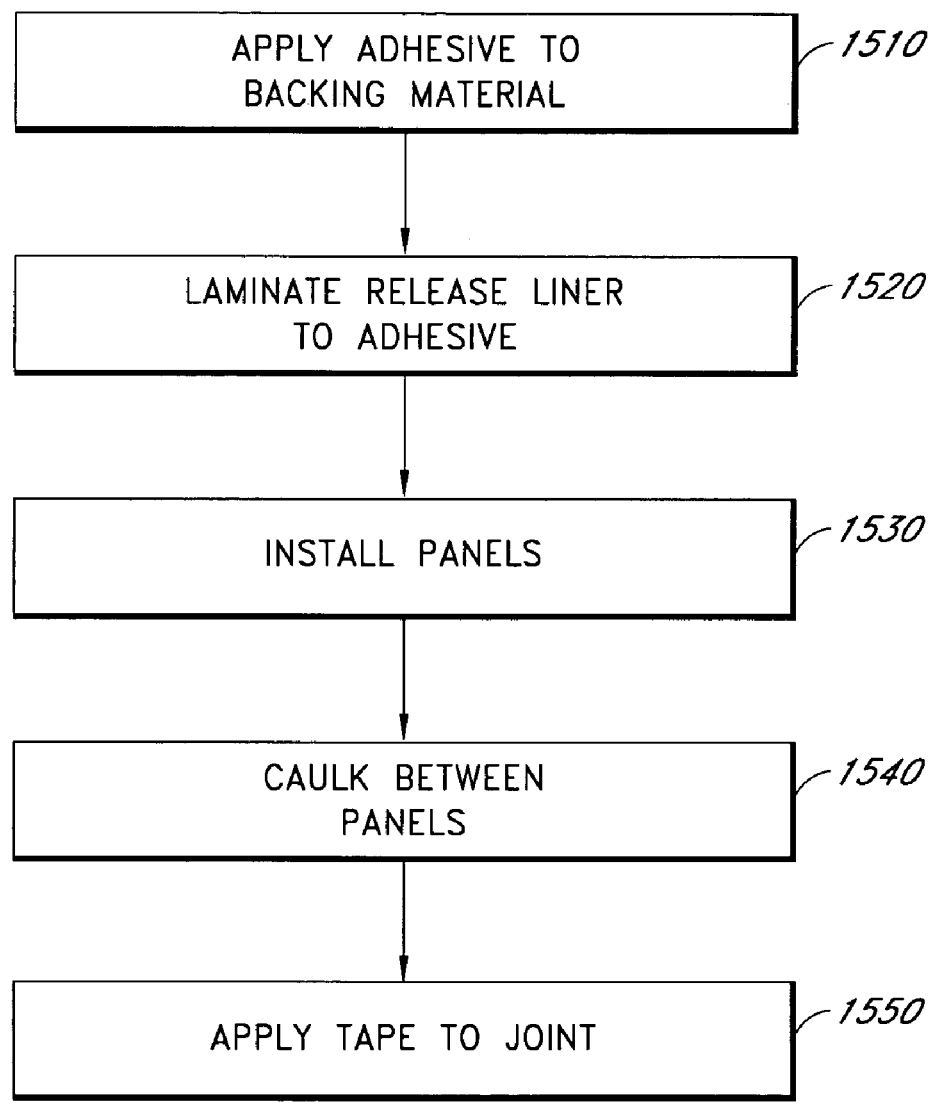
FIG. 15 is a flowchart illustrating METHOD 1 for making an elastomeric joint.
Figure 30:
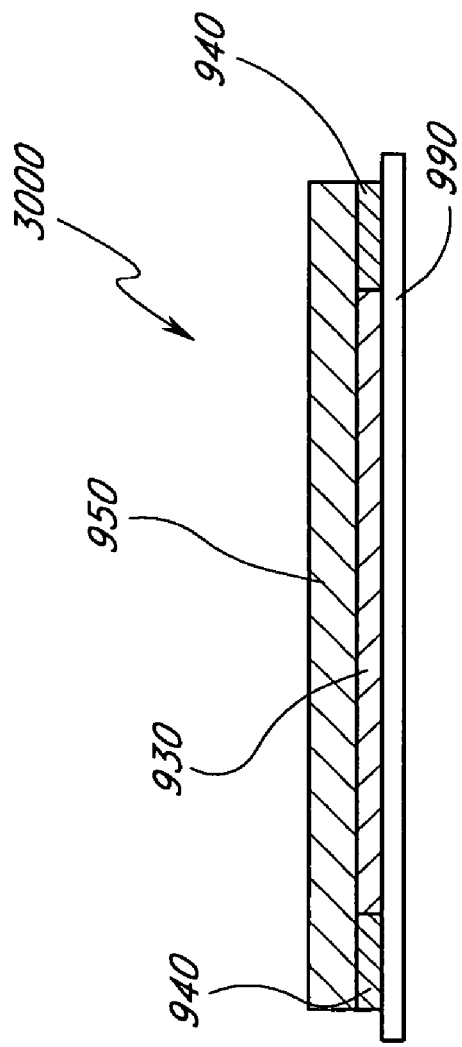
FIG. 30 is a cross section of a joint tape.

FIG. 30 illustrates a preferred embodiment of a joint tape 3000 made from a backing material 950, a first adhesive 930, a second adhesive 940, and an optional release liner 990. In METHOD 1 first adhesive 930 and the second adhesive 940 are the same adhesive. FIG. 15 illustrates METHOD 1 for fabricating an elastomeric joint in which the joint tape 3000 is manufactured in steps 1510 and 1520. The joint tape can be pre-made, for example, by a tape manufacturer.

In step 1510, an adhesive layer 930 is applied to a face of a backing material 950. A preferred adhesive is a pressure-sensitive adhesive, which may include a water-based, solvent-based, or 100% solid-based adhesive. More preferably, the adhesive is a 100%-solid, hot-melt adhesive that does not depend on water or solvent evaporation for curing. In step 1520, a paper or plastic film 990 coated with a release agent is optionally laminated to the adhesive layer of the joint tape. A preferred release agent is a silicone-based polymer. The thickness of release liner is preferably from about 0.0002" to about 0.005". The release liner is easy to be peeled from the adhesive layer in the application of the joint tape.

In step 1530, adjacent fiber cement panels 910 are installed as described above. Panels are preferably installed with a ⅛" gap between the panels to allow for building and panel movement. In another preferred embodiment, the panels 910 are butted together, leaving no gap.

In step 1540, caulk 920 is optionally applied between panels 910. The caulk is preferably applied flush with the surface of the panels 910. The caulk 920, preferably a high solids, non-shrinking, and permanently flexible caulk made from 100% solid urethane, provides a surface to which the joint tape adheres and provides an even surface, supporting the tape and stucco under tensile and compressive forces across the joint.

In step 1550, the release liner is removed from the elastomeric joint tape and the exposed adhesive face of the joint tape is applied over the joint between the panels 910. The joint tape is preferably centered over the joint. The nominal 3" elastomeric joint tape and flexible stucco finish are capable of withstanding significant joint movement without cracking the stucco finish.

Each the following examples uses a 3"-wide backing material or tape to allow direct comparison of the results. Other widths of backing material or tape may also be used.

EXAMPLE 5

Commercial Joint Tape

A commercially available elastomeric tape used in cementitious panel construction (Multicoat, Costa Mesa) is made from a fabric backing and a pressure-sensitive adhesive. The adhesive on this tape is about 0.01" thick. Two 2"×5" pre-coated fiber cement board specimens were arranged with a ⅛" gap between them. The gap was caulked with a 100% polyurethane caulk (Chem-calk 900, Bostik Findley), the caulk surface smoothed, and the caulk allowed to cure overnight. A 2"×3" piece of Multicoat elastomeric tape was centered and applied over the caulked joint. The test sample was finished with a medium texture coating (Multicoat, Costa Mesa, Calif.). The thickness of the texture coating was about 0 to ¹⁄₁₆", varying with the texture pattern on the surface.

The sample was equilibrated for 7 days at 72° F. at 50% relative humidity. The texture coating cracked when the joint was stretched about 3.5 to 4 mm (4.6–5.2%) at 6 mm/min at 72° F. At 120° F., the texture coating cracked when the joint was stretched 2 mm (2.6%). The cracking occurred at the edges of the tape because of slipping of the tape edges on the panels.

The joint was also tested statically. In a static test, the sample is rapidly stretched to a predetermined length (over a few seconds). The sample is held in the stretched state and the time required for the finish to crack measured. After stretching the joint about 2.5 mm (3.3%) at 72° F., the texture coating cracked after 2 minutes. Thus, joints made from the commercially available 3"-wide joint tape may not be strong enough to withstand the possible movement of 4'×8' cementitious panels.

The 180° peel strength of the Multicoat tape was 10.3 lb/inch at 72° F. At 120°F., the 180° peel strength was only about 1 lb/inch. Under water-saturation conditions, the 180° peel strength 4 lb/inch at 72° F. In each test, the test speed was 60 mm/min.

EXAMPLE 6

A joint tape was made with a 0.006"-thick layer of PL919 pressure-sensitive adhesive (SIA Adhesives) on 3"-wide piece of Sontara 8000 fabric (Dupont). Two 2"×5" primed cementitious fiber cement specimens were prepared and caulked as described in EXAMPLE 5. A 2"×3" piece of the joint tape was centered and applied to the joint. The tape was centered over the caulk joint. The test sample was finished and the finish cured as described EXAMPLE 5.

Under tensile testing at 6 mm/min, the texture coating did not crack until the joint was stretched about 10–12 mm (13.1–15.7%) at 72° F. The 3"-wide elastomeric joint tape prepared in this example is capable of withstanding greater than the expected normal movement of 4'×8' fiber cement panels.

The 180° peel strength of this tape was about 10.6 lb/inch at 72° F. At 120° F., the 180° peel strength was reduced to about 6.4 lb/inch. Under water saturation conditions, the 180° peel strength was about 7 lb/inch at 72° F. This joint tape had better heat and water resistance than the Multicoat tape used in EXAMPLE 5.

EXAMPLE 7

A joint tape was made with a 0.006"-thick layer of H400 pressure sensitive adhesive (Heartland Adhesives & Coatings) on 3"-wide piece of Sontara 8000 fabric (Dupont). Two 2"×5" pieces of primed fiber cement panel (James Hardie, Fontana, Calif.) were butted together, leaving no gap. A 2"×3" piece of the joint tape was centered and applied to the joint. The test sample was finished and the finish cured as described in EXAMPLE 5.

Under tensile testing at 6 mm/min, the texture coating did not crack until the joint was stretched about 7 mm (9.2%) at 72° F. The 3"-wide elastomeric joint tape prepared in this example is capable of withstanding greater than the expected normal movement of 4'×8' fiber cement panels.

The 180° peel strength of this tape was about 10 lb/inch at 72° F. At 120° F., the 180° peel strength was reduced to about 4.7 lb/inch. Under water saturation conditions, the 180° peel strength was about 10 lb/inch at 72° F. This joint tape has better heat and water resistance than the Multicoat tape used in EXAMPLE 5.

The joint tapes made according to the present disclosure produce a joint that is more resistant to cracking than one produced with the commercial tape at identical tape widths. The selected adhesives endow the disclosed joint tapes with superior heat and water resistance compared to the commercial joint tape. Because the normal expected movement of 4'×8' fiber cement panels is 3–5 mm or more (3.9–6.6% for a 3"-wide tape), and because a standard joint tape is about 3" wide, an elastomeric joint preferably withstands greater than 6.6% stretching without cracking, more preferably from about 6.6% to about 20% stretching, wherein the preferred range includes stretching values of 7%, 8%, 9%, 10%, 11%, 12%, 13%, 14%, 15%, 16%, 17%, 18%, 19%, and 20%.

The 180° peel strength at 72° F. is preferably about 10 lb/in or greater, more preferably about 10.3 lb/in or greater, most preferably about 10.6 lb/in or greater. At 120° F., the 180° peel strength is preferably about 2 lb/in or greater, more preferably about 4 lb/in or greater, most preferably about 6 lb/in or greater. Under water saturation conditions at 72° F., the 180° peel strength is preferably about 5 lb/in or greater, more preferably, about 6 lb/in or greater, most preferably about 7 lb/in or greater.

Method 2

Figure 16:
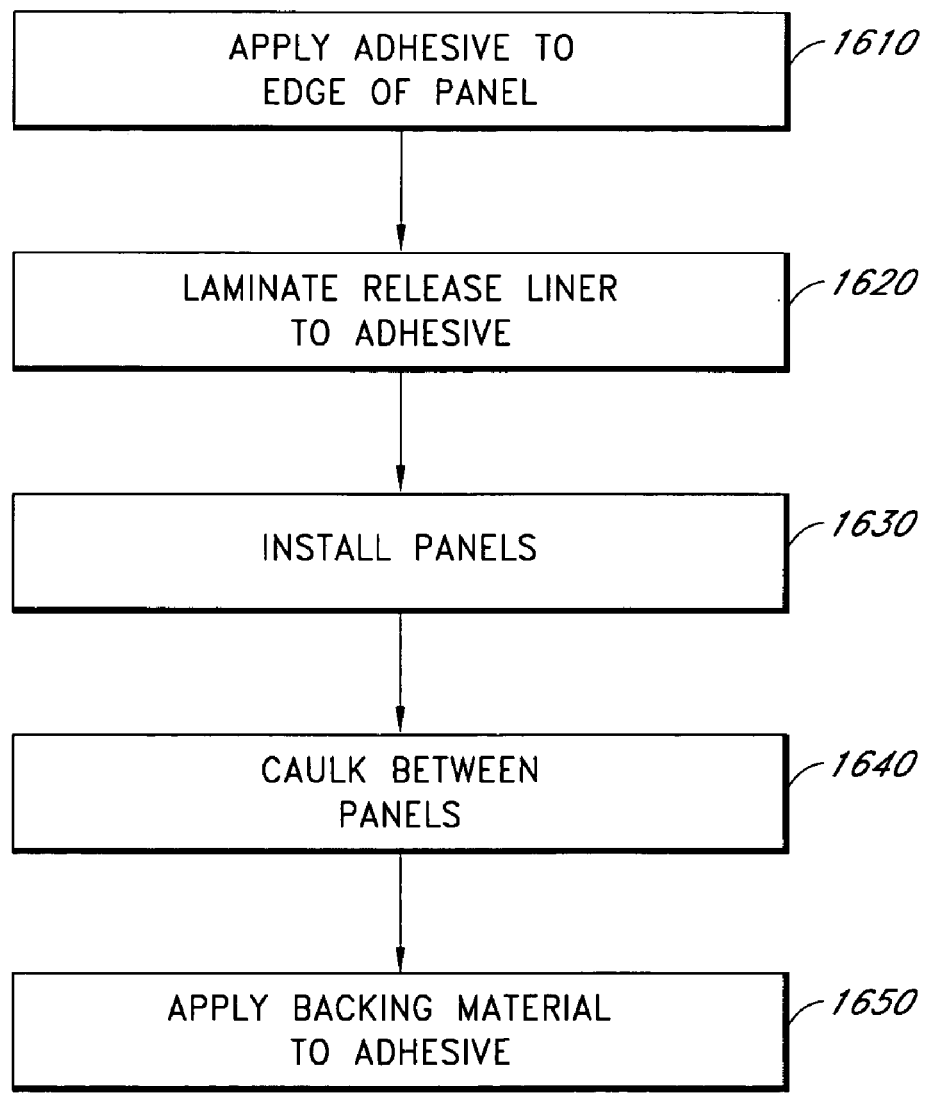
FIG. 16 is a flowchart illustrating METHOD 2 for making an elastomeric joint.
Figure 31A:
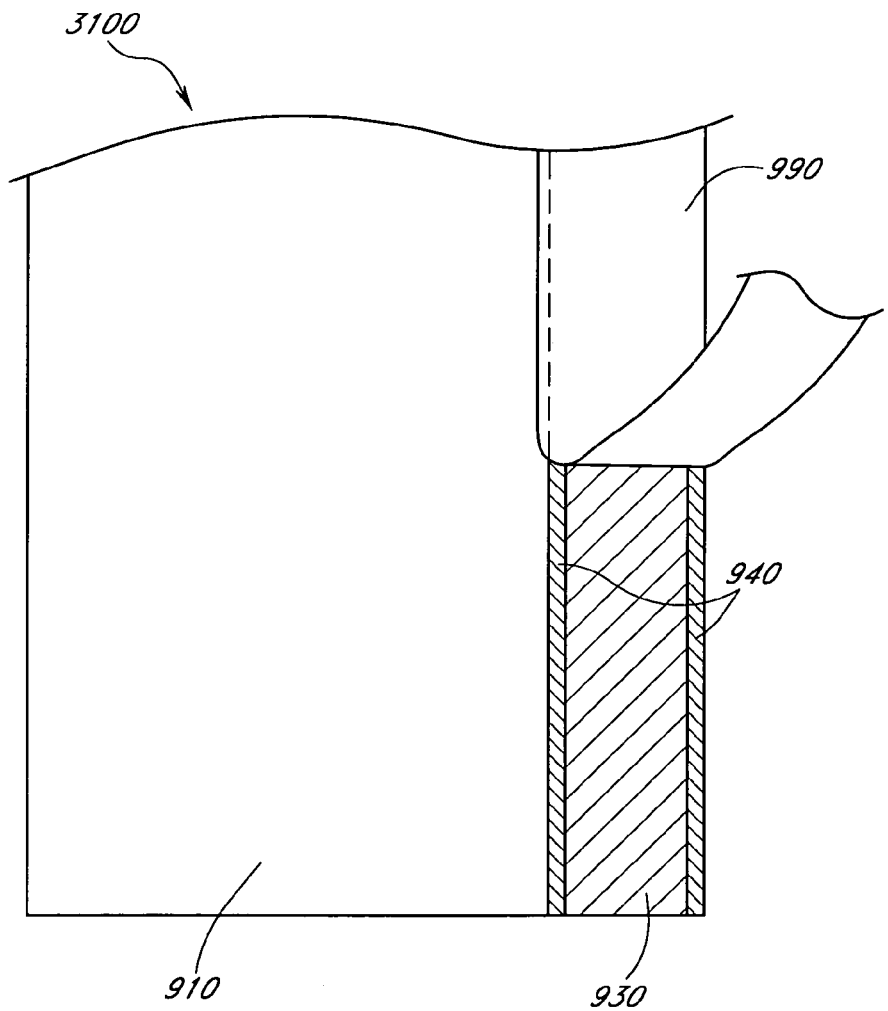
FIG. 31A and FIG. 31B are top and cross-sectional views of an adhesive-edge panel.
Figure 31B:
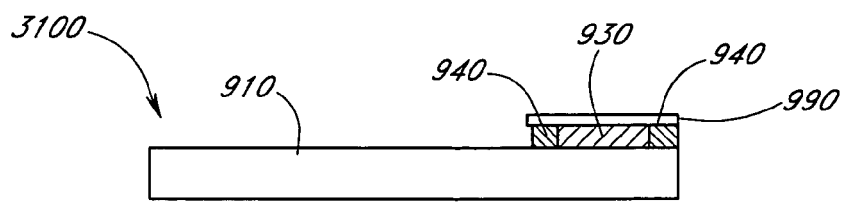

FIG. 16 illustrates METHOD 2 of making an elastomeric joint, which does not use an adhesive tape. A pressure-sensitive adhesive is applied to the edges of the front surface of building panels and a release liner laminated to the adhesive, producing adhesive-edge panels. A preferred embodiment of an adhesive-edge panel is illustrated in FIG. 31A and FIG. 31B, which has a panel 910, a first adhesive 930, a second adhesive 940, and a release liner 990. In METHOD 2, the first adhesive and the second adhesive are the same adhesive. The adhesive and release liner may be pre-applied by the panel manufacturer. The backing material is applied to the adhesive panels during wall installation. Steps 1610 and 1620 describe the manufacture of an adhesive-edge panel. Steps 1630, 1640, and 1650 describe making an elastomeric joint using the adhesive-edge panels.

In step 1610, an adhesive layer is applied along an edge of the front surface of a building panel. Specifications for the adhesive and methods of applying the adhesive are as described above. Preferably, the adhesive is applied around the perimeter of the front surface of the building panel. The width of the adhesive layer is preferably about one-half the width of the backing material, and may be adjusted to take into account any gaps to be left between adjacent panels or variability in the width of the backing material. The width of the adhesive layer may also be greater than one-half the width of the backing material to assure that the edges of the backing material are completely adhered to the panel and to allow for small misalignments in the installation of the backing material. An adhesive layer that is too wide increases amount of adhesive and release liner used, however, increasing the cost. Furthermore, foreign materials could potentially adhere to any adhesive that is not covered by the backing material, possibly affecting the appearance or adhesion of the finish layer. In a preferred embodiment for making a 3"-wide joint, an adhesive layer of from about 1⅜" to about 1 9/16", more preferably about 1 7/16" wide is applied at each edge.

In step 1620, a paper or plastic film coated with a release agent is laminated to the adhesive layer on the building panel. The specifications for the release liner are provided above. In step 1630, the panels are installed with the adhesive-coated faces facing outwards as described above. If gaps were left between the building panels, in step 1640, the gaps are optionally caulked as described above.

In step 1650, the release liner is removed from the adhesive and a backing material is applied to the adhesive.

Preferably, the backing material is centered over the joint. Suitable backing materials are described above.

EXAMPLE 8

A piece of 1 7/16"×2"×0.015" PL515 adhesive (SIA Adhesives) was applied to an edge of the upper surface of each of two 2"×5" primed fiber cement specimens (James Hardie, Fontana, Calif.). A sheet of silicone-based release liner was applied over the adhesive on each fiber cement specimen. The adhesive-coated edges were arranged face-up and adjacent, leaving a 1/8" gap between the specimens. The joint was caulked and the caulk cured as described in EXAMPLE 5. Then the release liner was from the adhesive on the fiber cement specimens. A 2"×3" piece of Sontara 8000 fabric (Dupont) was centered and applied to the adhesive. The test sample was finished and cured as described for EXAMPLE 5.

Under tensile testing at 6 mm/min, the texture coating did not crack until the joint was stretched about 12 mm (15.7%) at 72° F. The 3"-wide elastomeric joint prepared in this example is capable of withstanding greater than the expected normal movement of 4'×8' fiber cement panels.

Method 3

Figure 17:
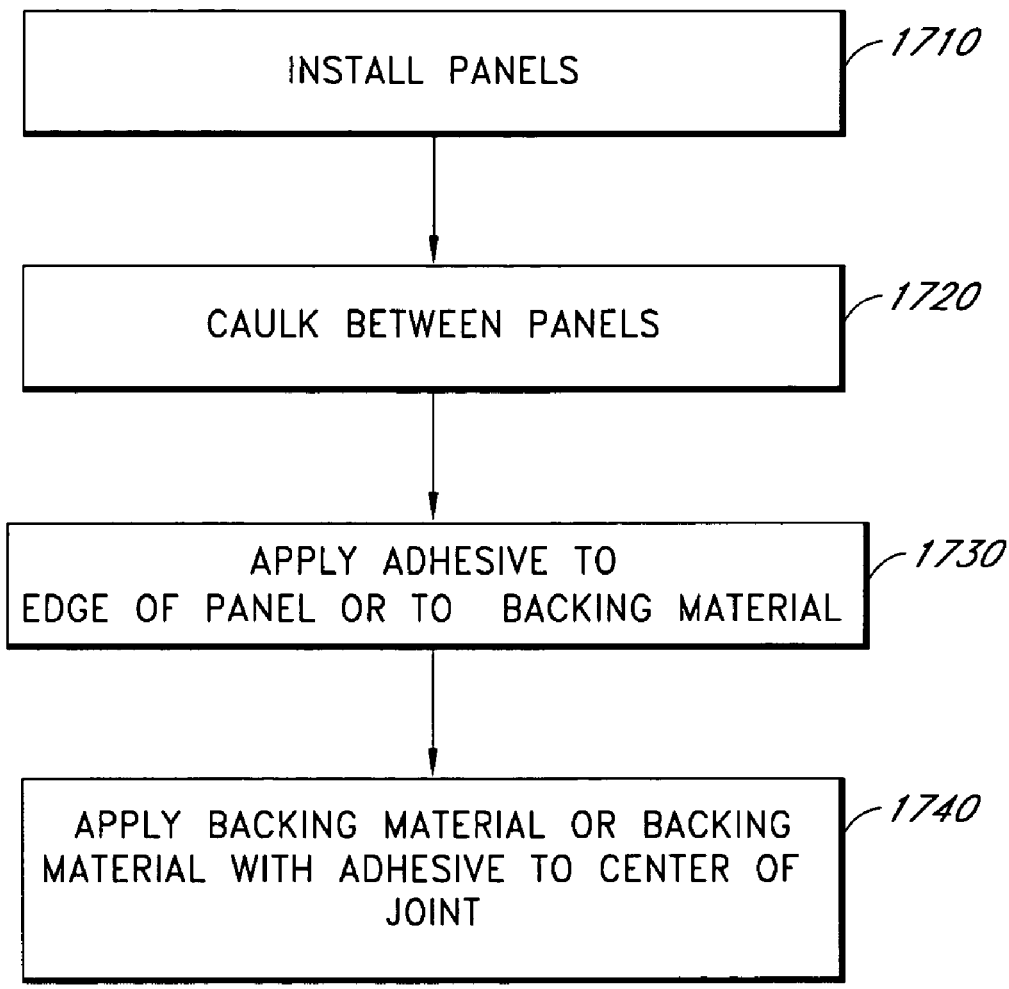
FIG. 17 is a flowchart illustrating METHOD 3 for making an elastomeric joint.

FIG. 17 illustrates METHOD 3 for making an elastomeric joint, in which neither an adhesive tape nor an adhesive panel is prefabricated. Instead, a flexible adhesive layer is applied either to the building panel or to the backing material after the panels have been installed onto a frame. The adhesive may be pressure sensitive or non-pressure sensitive. Preferably, the adhesive is non-pressure sensitive, resulting in a more durable joint. Typically, non-pressure-sensitive adhesives are more heat and water resistant than pressure-sensitive adhesives. The adhesive layer may be pre-made as a double-sided tape or an adhesive paste. In any case, the adhesive should distribute movement of the panels to the entire backing material, yet not slip from the panel at the edges of the backing material.

In step 1710, the panels are installed as described above. In step 1720, the panels are caulked as described above.

In step 1730, an adhesive layer is be applied either to the adjacent edges of the panels or to a backing material. Suitable adhesives and methods of applying the adhesive are described above. Preferred adhesives may be the same as or different from the preferred adhesives used in METHOD 1 or METHOD 2.

In step 1740, either the backing material is applied to the adhesive-covered edges of the panels or the adhesive-coated backing material to the center of the joint. A suitable backing material is selected as described above. If the adhesive is not a pressure-sensitive adhesive, this step is preferably completed before the adhesive cures excessively.

EXAMPLE 9

Two 2"×5" pre-coated fiber cement board specimens (James Hardie, Fontana, Calif.) were arranged with a 1/8" gap between them. The gap was caulked with a 100% polyurethane caulk (Chem-calk 900, Bostik Findley) and the caulk surface smoothed. In this example, the caulk was also used as the adhesive. A 0.01" layer of the same caulk was applied to a 2"×3" area centered on the joint. A 2"×3" piece of Sontara 8004 fabric (Dupont) was applied over the caulking. The test sample was finished and the finish cured as described in EXAMPLE 5.

Under tensile testing at 6 mm/min, the texture coating did not crack until the joint was stretched about 5.2–6.9 mm (6.8–9.1%) at 72° F.

Multiple adhesives may be used in the disclosed elastomeric joint system. In one embodiment, a first adhesive, applied at the center of the joint, is an elastomeric material that slips with the movement of the panels, distributing the movement to the entire backing material. A second adhesive, used at the edges of the joint, is relatively rigid, anchoring the edges of the backing material to the panel. An elastomeric joint made according to this method can withstand large relative panel movements without cracking the finish coating at any part of the joint, including the edges.

Method 4

Figure 18:
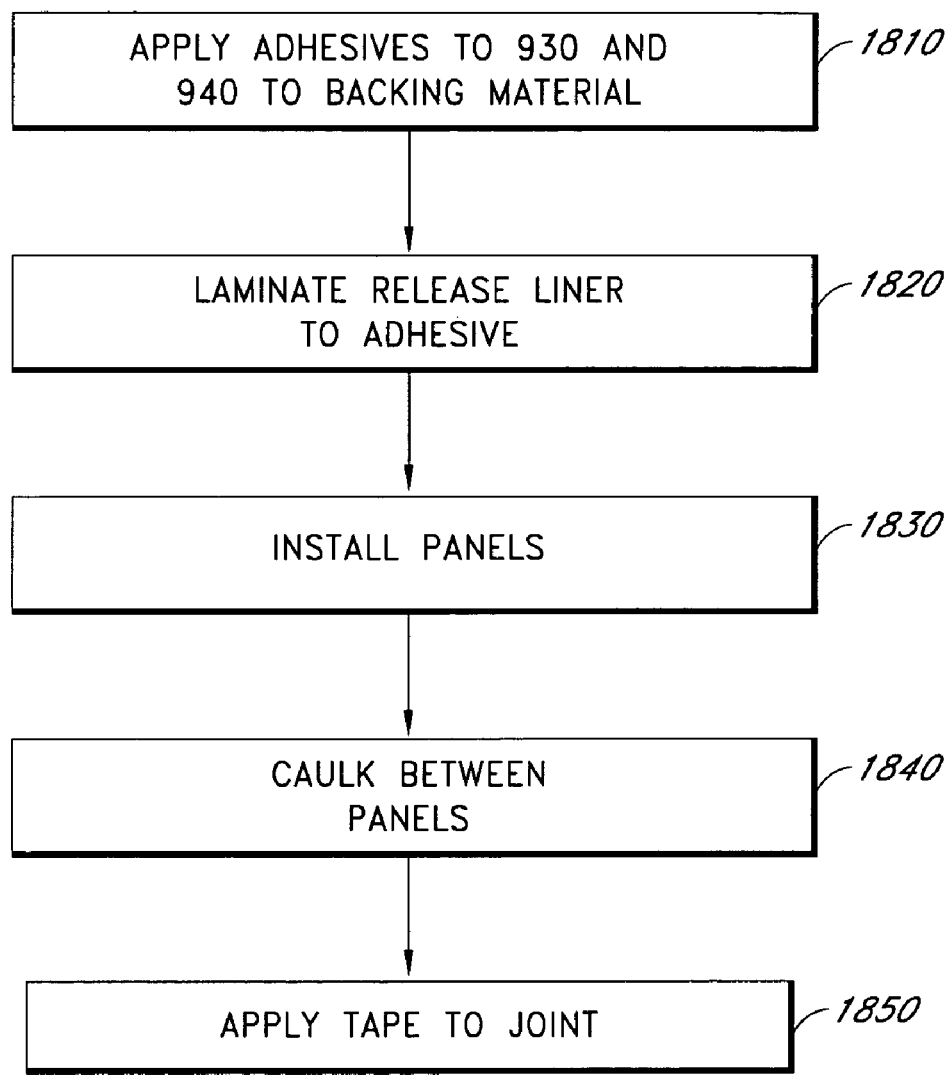
FIG. 18 is a flowchart illustrating METHOD 4 for making an elastomeric joint.

FIG. 30 illustrates a preferred embodiment of a joint tape 3000 made from a backing material 950, a first adhesive 930, a second adhesive 940, and an optional release liner 990. FIG. 18 illustrates METHOD 4, which like METHOD 1 uses a prefabricated adhesive joint tape. The joint tape may be prefabricated by a tape manufacturer. Unlike METHOD 1, the joint tape of METHOD 4 uses two adhesives, a first adhesive 930 used in the center, which is relatively elastomeric, and a second adhesive 940 used at the edges, which is relatively rigid. Preferred adhesives are pressure sensitive. For a 3"-wide tape, a preferred width of adhesive 930 is from about 0" to about 3" and a preferred width of adhesive 940 is from about 0" to about 3".

The steps of METHOD 4 are substantially the same as for METHOD 1. The principal difference between METHOD 4 and METHOD 1 is that METHOD 4 uses two adhesives where METHOD 1 uses a single adhesive.

A joint tape is made in steps 1810 and 1820. In step 1810, a first adhesive 930 and a second adhesive 940 are applied to a backing material 950. In step 1820, a release liner is optionally laminated to the adhesives.

In steps 1830, 1840 and 1850, the joint tape is applied to the seam between adjacent building panels to produce an elastomeric joint. In step 1830, building panels are installed as described above. In step 1640, caulk is optionally applied between the building panels, as described above. In step 1850, the release liner is removed from the elastomeric joint tape and the exposed adhesive face of the joint tape is applied over the joint between the panels. The joint tape is preferably centered over the joint.

EXAMPLE 10

A tape was made with PVT-3300 (Carlisle Coating & Waterproofing) and HL 2203 (H.B. Fuller) pressure sensitive adhesives. A 2½"-wide×0.028"-thick layer of PVT-3300 adhesive was applied to the center of a 3"-wide strip of Sontara 8000 fabric (Dupont). A ¼"-wide×0.002"-thick layer of HL 2203 adhesive was applied to both edges of the fabric. Two 2"×5" primed fiber cement specimens (James Hardie, Fontana, Calif.) were butted together with no gap and no caulk. A 2"×3" piece of the elastomeric tape was centered over the seam and applied to the panels. The test sample was finished and the finish cured as described in EXAMPLE 5.

Under tensile testing at 6 mm/min, the texture coating did not crack until the joint was stretched about 12–13 mm (15.7–17.1%) at 72° F. The 3"-wide elastomeric joint tape prepared in this example is capable of withstanding greater than the expected normal movement of 4'×8' fiber cement panels.

EXAMPLE 11

The experiment of EXAMPLE 10 was repeated except that the tape was made with only the elastomeric first adhesive. In this example, a 3"-wide×0.028"-thick layer of PVT-3300 pressure sensitive adhesive was used to make the joint tape. No H2203 adhesive was used at the edge. Under the same test conditions, the texture coating cracked at the edge of the fabric when the joint was stretched about 3–4 mm (3.9–5.2%) at 72° F.

EXAMPLE 10 and EXAMPLE 11 demonstrate the advantages of a dual-adhesive system compared to a similar single-adhesive system.

Note that in EXAMPLE 10 and EXAMPLE 11, the elastomeric joint is fabricated without caulk, i.e., the joint is a caulkless elastomeric joint. This caulkless joint has several advantages over a joint made with caulk. First, omitting the caulk is less expensive because one need not obtain the caulk. Second, the caulkless method saves the time required to apply the caulk as well as the time required for the caulk to cure. Third, the caulkless method is simpler, both because one need not apply any caulk, and because the panels may be butted together, eliminating the step of positioning the panels with gaps.

Method 5

Figure 19:
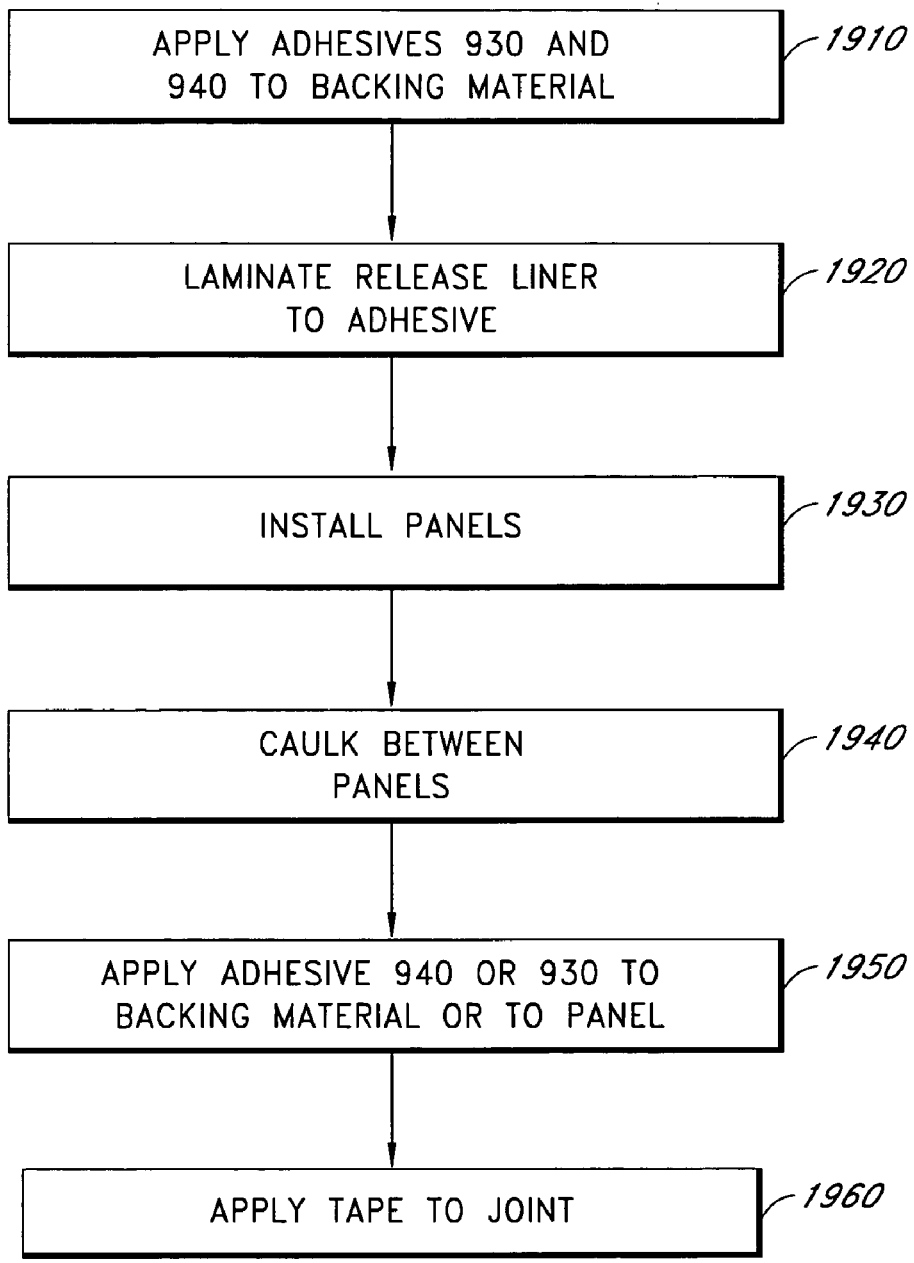
FIG. 19 is a flowchart illustrating METHOD 5 for making an elastomeric joint.

FIG. 19 illustrates METHOD 5 of making an elastomeric joint. As in METHOD 1 and METHOD 4, a joint tape is prefabricated, then applied to the joint. In a preferred embodiment, the joint tape is pre-made by a tape manufacturer. Unlike the joint tape of METHOD 4, which is a dual adhesive tape, the joint tape of METHOD 5 is a single adhesive tape. The adhesive 930 in the joint tape of METHOD 5 is pre-applied down the center of the backing material, with no adhesive at the edges. The second adhesive 940 is applied during the installation of the wall system either to the backing material or to the building panels.

In an alternative embodiment, the joint tape is prefabricated with the second adhesive 940 applied to the edges of the backing material. In this embodiment, the first adhesive 930 is applied during the installation of the wall system either to the center of the baking material or to the building panels.

Preferably, the adhesive applied to the backing material in the joint tape manufacturing process is pressure sensitive. The adhesive applied during the installation of the wall system may be pressure sensitive or non-pressure sensitive. More preferably, the joint tape is manufactured with the first adhesive 930, the more elastomeric adhesive, applied down the center of the backing material. In this embodiment, the second adhesive 940 is preferably a non-pressure-sensitive adhesive because a wider range of non-pressure-sensitive adhesives produce the desired strong bond between the panel and the edges of the backing material. For a 3"-wide tape, the preferred width of adhesive 930 is from about 0" to about 3", and the preferred width of adhesive 940 is from about 0" to about 3", wherein the sum of the widths of the two adhesives is 3". The following procedure describes an embodiment in which the first adhesive 930 is used to manufacture the joint tape.

The joint tape is manufactured in steps 1910 and 1920. In step 1910, first adhesive 930 is applied down the center of the adhesive 950. Selection of adhesive and the backing material, and application of the adhesive is described above. In step 1920, a release liner is optionally laminated to the adhesive.

In step 1930, building panels are installed as described above. In step 1940, caulk is optionally applied between the building panels, as described above. In step 1950, second adhesive 940 is applied to the panel at a location corresponding to the edges of the installed backing material or applied to the edges of the backing material of the joint tape manufactured in steps 1910 and 1920. The second adhesive 940 is applied as described above. Preferably, the second adhesive 940 is non-pressure sensitive. The second adhesive 940 may be applied either before or after the joint tape has applied to the joint.

EXAMPLE 12

A 2½"-wide×0.028"-thick layer of PVT-3300 pressure sensitive adhesive (Carlisle Coating & Waterproofing) was applied down the center of a 2"×3" piece of Sontara 8000 fabric (Dupont), leaving about a ¼" of each 2" edge of the fabric was free of adhesive. Two 2"×5" specimens of primed fiber cement panels were butted together, leaving no gap. No caulk was applied. The elastomeric joint tape was centered and applied to the joint. To each edge of the backing material was applied a ¼"-wide×0.002"-thick layer of UR-0210 moisture-cured polyurethane (H.B. Fuller), and the edges applied to the panels. The test sample was finished and the finish cured as described in EXAMPLE 5.

Under tensile testing at 6 mm/min, the texture coating did not crack until the joint was stretched about 12–13 mm (15.7–17.1%) at 72° F. At 120° F., the texture coating cracked when the joint was stretched 13 mm (17.1%), indicating the heat resistance of the joint. The 3"-wide elastomeric joint tape prepared in this example is capable of withstanding greater than the expected normal movement of 4'×8' fiber cement panels.

The Sontara fabrics (Dupont) work well as the backing material, although other stretchable fabrics are also suitable. The experiment in EXAMPLE 12 was repeated with a polyamide (Nylon) fabric in EXAMPLE 13.

EXAMPLE 13

A 2½"-wide×0.028"-thick layer of PVT-3300 pressure sensitive adhesive was applied down the center of a 3"-wide piece of Nylon mesh P2017 (Applied Extrusion Technologies), leaving about a ¼" of each 2" edge of the fabric was free of adhesive. Two 2"×5" specimens of primed fiber cement panels were butted together, leaving no gap. No caulk was applied. The elastomeric joint tape was centered and applied to the joint. To each edge of the backing material was applied a ¼"-wide×0.002"-thick layer of UR-0210 moisture-cured polyurethane (H.B. Fuller), and the edges applied to the panels. The test sample was finished and the finished cured as described in EXAMPLE 5.

Under tensile testing at 6 mm/min, the texture coating did not crack until the joint was stretched about 7–11 mm (9.2–14.4%) at 72° F. The 3"-wide elastomeric joint tape prepared in this example is capable of withstanding greater than the expected normal movement of 4'×8' fiber cement panels.

Non-stretchable and semi-stretchable fabrics such as non-woven glass fiber fabric that were tested were unable to withstand large joint movements. A representative test is provided in EXAMPLE 14.

EXAMPLE 14

A 2½"-wide×0.028"-thick layer of PVT-3300 pressure sensitive adhesive (Carlisle Coating & Waterproofing) was applied down the center of a 3"-wide piece of non-woven glass-fiber fabric (M524-C33, Owens Corning) leaving about a ¼" of each 2" edge of the fabric was free of adhesive. Two 2"×5" specimens of primed fiber cement panels were butted together, leaving no gap. No caulk was applied. The elastomeric joint tape was centered and applied to the joint. To each edge of the backing material was applied a ¼"-wide×0.002"-thick layer of UR-0210 moisture-cured polyurethane (H.B. Fuller), and the edges applied to the panels. The test sample was finished and the finish cured as described in EXAMPLE 5.

Under tensile testing at 6 mm/min, the texture coating cracked when the joint was stretched about 1.8 mm (2.4%) at 72° F. The 3"-wide joint tape prepared in this example is incapable of withstanding greater than the expected normal movement of 4'×8' fiber cement panels.

Method 6

Figure 20:
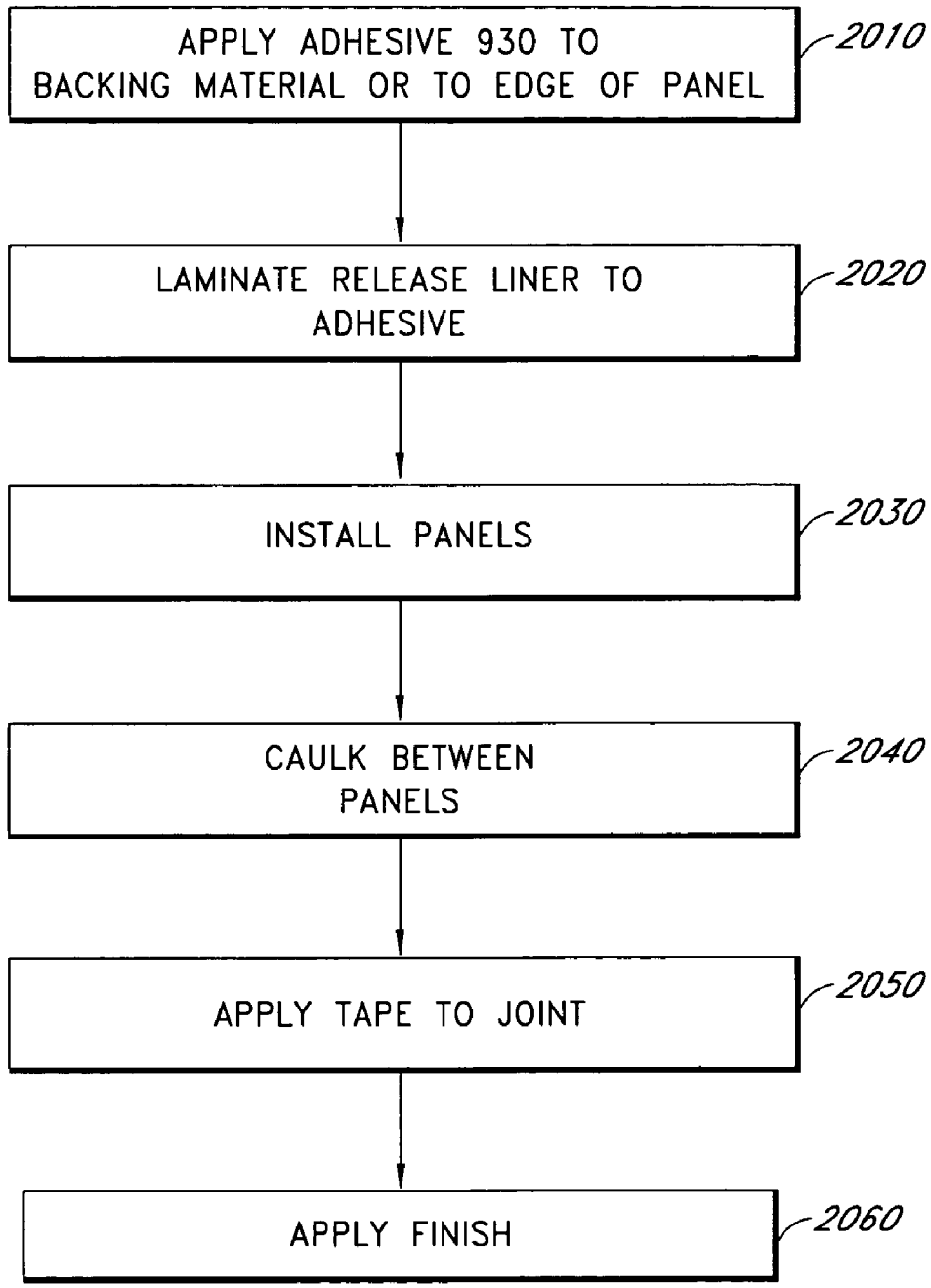
FIG. 20 is a flowchart illustrating METHOD 6 for making an elastomeric joint.

FIG. 20 illustrates METHOD 6 of making an elastomeric joint, which is similar to METHOD 5, except that the second adhesive 940 is not applied to the backing material or panels in a step analogous to step 1950 of METHOD 5. Instead, METHOD 6 uses a backing material that allows the finish coating to permeate the fabric and to bond to the building panels. As such, the finish coating serves as the second adhesive 940, eliminating a separate application step. For a 3"-wide tape, the preferred width of adhesive 930 is from about 0" to about 3".

In step 2010, first adhesive 930 is applied down the center of the backing material 950. The backing material is permeable to the elastomeric finish coat. Selection and application of the adhesive is described above. In step 1820, a release liner is optionally laminated to the adhesive 930.

In step 2030, building panels are installed as described above. In step 2040, caulk is optionally applied between the building panels, as described above. In step 2050, the release liner is removed from the elastomeric joint tape and the exposed adhesive face of the joint tape is applied over the joint between the panels. The joint tape is preferably centered over the joint. In step 2060, an elastomeric finish 980 is applied to the panelized wall system. The finish permeates the backing material 950, functioning as the second adhesive 940.

In alternative embodiment of METHOD 6, a strip of the first adhesive 930 that is narrower than the backing material is applied to adjacent edges of the building panels. A backing material that is permeable to the elastomeric finish coating is then centered and applied to the joint, leaving the edges of the backing material free of adhesive. The texture coating applied to the entire wall permeates the backing material, functioning as the second adhesive 940. For 3"-wide backing material, the preferred width of adhesive 930 is from about 0" to about 3". Where the first adhesive 930 is 3"-wide, the same width as the backing material, METHOD 6 is the same as METHOD 1.

EXAMPLE 15

A 2½"-wide×0.028"-thick layer of PVT-3300 pressure sensitive adhesive (Carlisle Coating & Waterproofing) was applied down the center of a 3"-wide piece of Sontara 8801 fabric (Dupont), leaving about a ¼" of each 2" edge of the fabric was free of adhesive. Two 2"×5" specimens of primed fiber cement panels were arranged with a ⅛" gap. No caulk was applied to the gap. The elastomeric joint tape was centered and applied to the joint. The test sample was finished and the finish cured as described in EXAMPLE 5.

Under tensile testing at 6 mm/min, the texture coating did not crack until the joint was stretched about 9–13 mm (11.8–17.1%) at 72° F. The 3"-wide elastomeric joint tape prepared in this example is capable of withstanding greater than the expected normal movement of 4'×8' fiber cement panels.

Method 7

Figure 21:
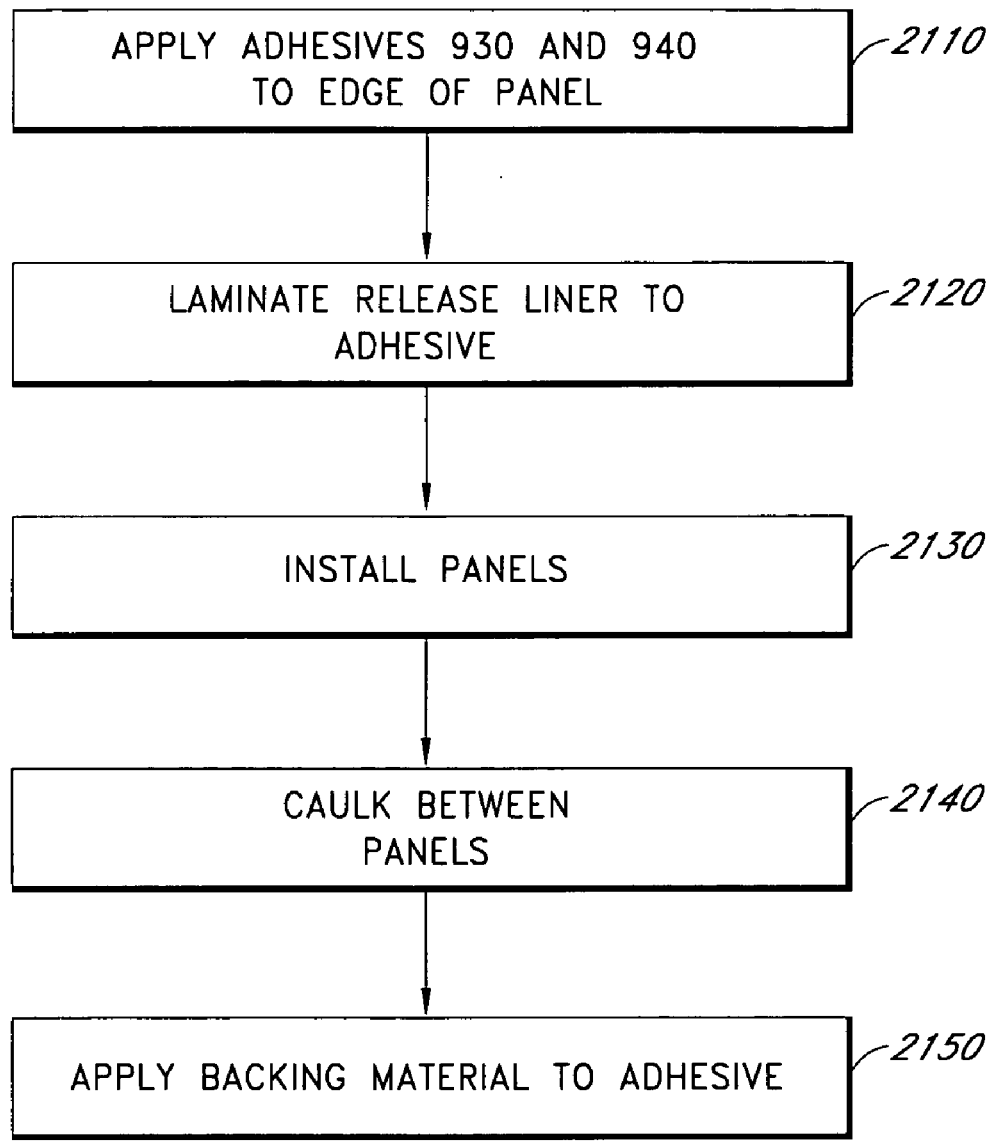
FIG. 21 is a flowchart illustrating METHOD 7 for making an elastomeric joint.

FIG. 21 illustrates METHOD 7 for making an elastomeric joint, which is similar to METHOD 2 in that an adhesive joint tape is not pre-made. Instead, pressure-sensitive adhesives are applied to the edges of the front faces of the building panels and a release liner is laminated to these adhesive-edge panels. The adhesive-edge panels may be prefabricated by the panel manufacturer. After the panels are fastened to the frame, the backing material is applied to the adhesive of adjacent panels. A preferred embodiment of an adhesive-edge panel is illustrated in FIG. 31A and FIG. 31B, which has a panel 910, a first adhesive 930, a second adhesive 940, and a release liner 990. Unlike METHOD 2, which uses a single adhesive, METHOD 7 uses two adhesives, a more elastomeric first adhesive 930, applied at the center of the joint, and a more rigid second adhesive 940, applied at the edges of the joint. Preferably, both adhesives 930 and 940 are pressure sensitive.

For a 3"-wide backing material, the preferred width of adhesive 930 on each panel is from about 0" to about 1½" and the preferred width of adhesive 940 on each panel is from about 0" to about 1½", wherein the sum of the widths is about 1½". As would be apparent to one skilled in the art, the sum of the widths may be smaller if adjacent panels are installed with a gap. METHOD 7 is the same as METHOD 2 if the width of either the first adhesive 930 or the second adhesive 940 is 0".

In step 2110, a first adhesive 930 is applied along an edge of the front surface of a building panel and a second adhesive 940 is applied adjacent to the first adhesive 930, away from the edge of the panel. Specifications for the adhesives and methods of applying the adhesive are as described above. Preferably, the adhesive is applied around the perimeter of the front surface of the building panel. In a preferred embodiment, the total width of the adhesive layers is about 1⁷⁄₁₆" wide at the edge for making a 3"-wide elastomeric joint.

In step 2120, a release liner is laminated to the adhesive layer on the building panel. The specifications for the release liner are provided above.

In step 2130, the panels are installed with the adhesive-coated faces facing outwards as described above. In step 2140, the gaps between the installed building panels are optionally caulked as described above. In step 2150, the release liner is removed and the backing material is applied to the exposed adhesive. Preferably, the backing material is centered over the joint. Suitable backing materials are described above.

EXAMPLE 16

The same methods and materials used in EXAMPLE 10 (METHOD 4) were used in EXAMPLE 16, except that the adhesives were applied to the fiber cement panels instead of to the backing material. Under tensile testing at 6 mm/min, the texture coating did not crack until the joint was stretched about 12–13 mm (15.7–17.1%) at 72° F. The 3"-wide elastomeric joint prepared in this example is capable of withstanding greater than the expected normal movement of 4'×8' fiber cement panels.

Method 8

Figure 22:
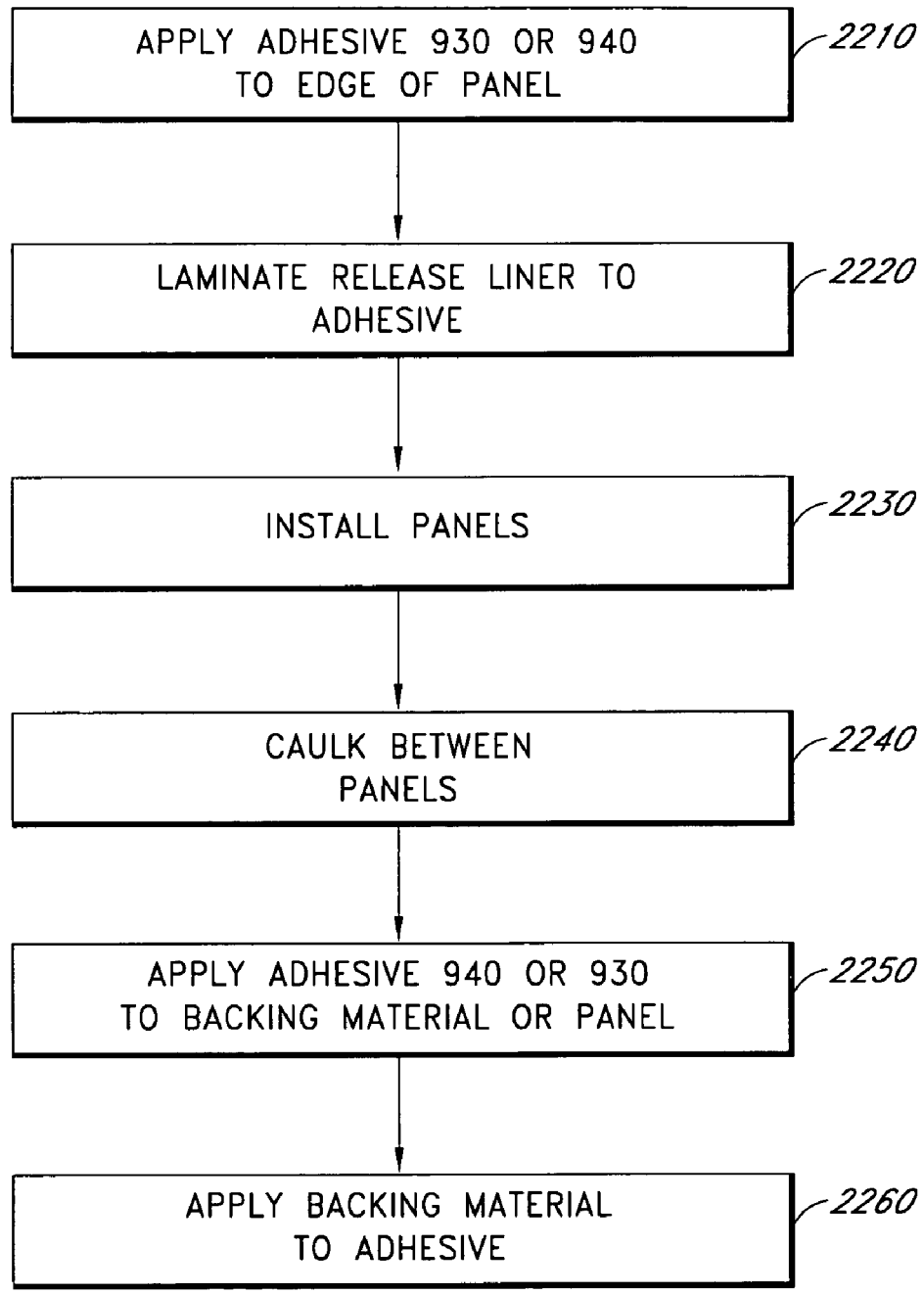
FIG. 22 is a flowchart illustrating METHOD 8 for making an elastomeric joint.

FIG. 22 illustrates METHOD 8 of making an elastomeric joint, which is similar to METHOD 7 except that only one adhesive is pre-applied to the building panels. The adhesive may be pre-applied by the panel manufacturer.

In METHOD 8, a first adhesive 930 is applied to the part of the edge on the front face of a panel that will become the center of the joint. The second adhesive 940 is applied either to the backing material or to the part of the panel corresponding to the edge of the joint during wall installation. In another embodiment, the second adhesive 940 is pre-applied to the panel before installation, and first adhesive 930 is applied to the backing material or to the panel during the wall installation. Preferably, the pre-applied adhesive is pressure sensitive. The later applied adhesive may be pressure sensitive or non-pressure sensitive. More preferably, first adhesive 930 is the pre-applied adhesive and second adhesive 940 is the later applied adhesive. In this embodiment, the second adhesive 940 is preferably a non-pressure-sensitive adhesive because a wider range of non-pressure-sensitive adhesives produce the desired strong bond between the panel and the edges of the backing material. For a 3"-wide joint, the preferred width of the first adhesive 930 on each panel is from about 0" to 1½", and the preferred width of the second adhesive 940 on each panel is about 0 to 1½", wherein the sum of the widths about 1½".

In step 2210, a first adhesive 930 is applied along an edge of the front surface of a building panel to an area corresponding to the center of the joint. Specifications for the adhesives and methods of applying the adhesive are as described above. Preferably, the adhesive is applied around the perimeter of the front surface of the building panel. In a preferred embodiment, the total width of the adhesive layers is about 1 7/16" wide at the edge for making a 3"-wide elastomeric joint.

In step 2220, a release liner is laminated to the adhesive layer on the building panel. The specifications for the release liner are provided above.

In step 2230, the panels are installed with the adhesive-coated faces facing outwards as described above. In step 2240, the gaps between the installed building panels are optionally caulked as described above. In step 2250, a second adhesive 940 is applied to the edges of a backing material 950 or to the portion of the panel corresponding 910 to the edge of the joint. In step 960, the release liner is removed and the backing material is applied to the exposed adhesive. Preferably, the backing material is centered over the joint. Suitable backing materials are described above.

In an alternative embodiment, the second adhesive 940 is applied in step 2010 to the area on an edge of the panel 910 corresponding to the edge of the joint. In step 950, the first adhesive 930 is applied to either the center of the backing material 950 or to the portion of the panel 91 0 corresponding to the center of the joint.

Method 9

Figure 23:
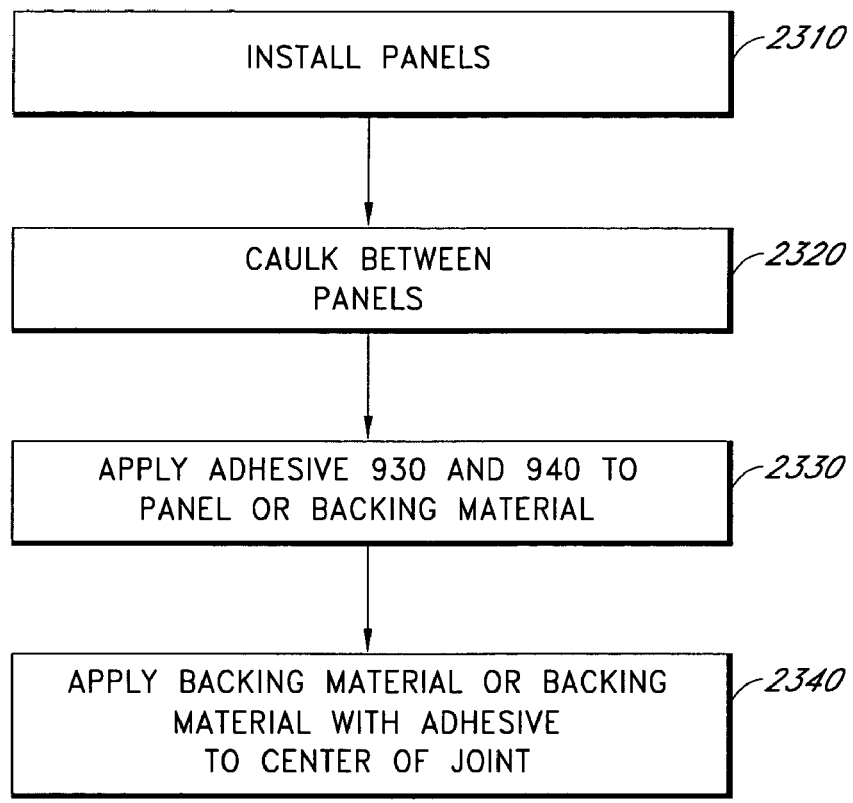
FIG. 23 is a flowchart illustrating METHOD 9 for making an elastomeric joint.

FIG. 23 illustrates METHOD 9 of making an elastomeric joint, which is similar to METHOD 3 in that adhesive is not pre-applied either to the backing material or to the panels. The difference between METHOD 9 and METHOD 3 is that METHOD 9 uses two adhesives while METHOD 3 uses a single adhesive. The adhesives may be applied either to the backing material or to the panels. Either adhesive layer may be made into a double-side tape or an adhesive paste. In another embodiment, both adhesives are incorporated into a single double-sided tape. For a 3"-wide joint, the preferred width of the first adhesive 930 is from about 0" to about 3" and the preferred width of the second adhesive 940 is from about 0" to about 3", wherein the sum of the widths of the two adhesives is about 3".

In step 2310, the panels are installed as described above. In step 2320, caulk is optionally applied to any gaps left between the panels.

In step 2330, a first adhesive 930 and a second adhesive 940 are applied to a backing material 950 or to the area of the panels 910 corresponding to the joint. In either case, the first adhesive 930 is applied to the area corresponding to the center of the joint and the second adhesive is applied to the area corresponding to the edges of the joint. The first adhesive 930 may be applied before, after, or at same time as the second adhesive 940.

In step 2340 the backing material with the preapplied adhesive is applied to the joint between adjacent panels, or a backing material is applied to the adhesive that was preapplied to the panels. Preferably, the backing material is centered over the joint in either case.

EXAMPLE 17

Two 2"×5" specimens of primed fiber cement panels were arranged with a ⅛" gap between them. The gap was caulked and the caulk cured as described in EXAMPLE 5. A 2½"-wide×0.02"-thick layer of HL2203 adhesive (H.B. Fuller) was applied to the panels centered on the joint. A /1;4"-wide×0.002"-thick layer of UR-0210 moisture-cured polyurethane adhesive (H.B. Fuller) was applied on the panels on each side of the HL2203 adhesive. A 2"×3" piece of Sontara 8000 fabric was applied to the adhesives. The test sample was finished and the finish cured as described in EXAMPLE 5.

Under tensile testing at 6 mm/min, the texture coating did not crack until the joint was stretched about 16 mm (21.0%) at 72° F. The 3"-wide elastomeric joint prepared in this example is capable of withstanding greater than the expected normal movement of 4'×8' fiber cement panels.

Method 10

Figure 24:
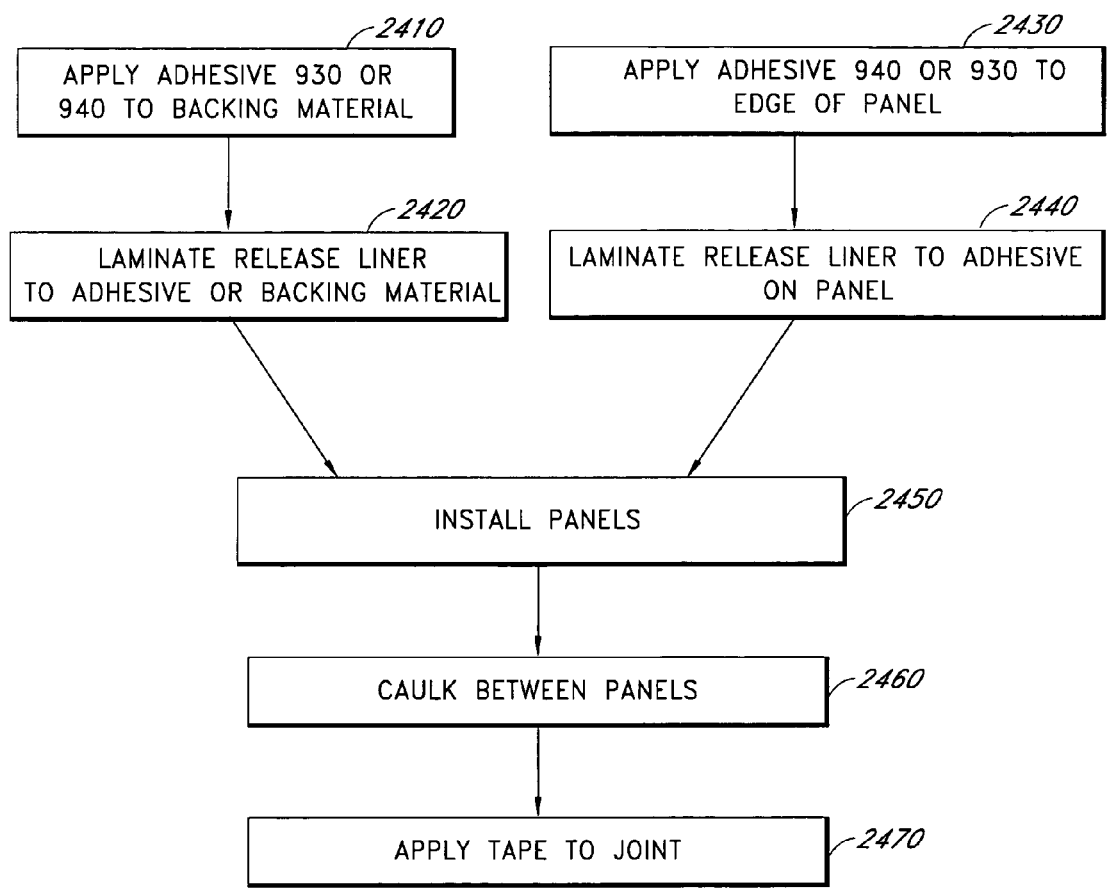
FIG. 24 is a flowchart illustrating METHOD 10 for making an elastomeric joint.

FIG. 24 illustrates METHOD 10 of making an elastomeric joint, which uses both an adhesive joint tape and adhesive-edge panels. The first adhesive 930 is pre-applied either to the backing material or to an edge of the front of the panel. The second adhesive 940 is pre-applied to an edge of the front of the panel if the first adhesive is pre-applied to the backing material, or to the backing material if the first adhesive is pre-applied to a edge of the front of the panel. Both adhesives are preferably pressure sensitive. For a 3"-wide joint, the preferred width of the first adhesive 930 is from about 0" to about 3" and the preferred width of the second adhesive 940 is from about 0" to about 3", wherein the sum of the widths of both adhesives is about 3". METHOD 10 is the same as METHOD 4 if both adhesives are pre-applied to the backing material and METHOD 7 if both adhesives are pre-applied to the front edges of the building panel.

In step 2410, a first adhesive 930 is applied down the center of the backing material 950. In step 2420, a release liner is optionally laminated to the first adhesive.

In step 2430, a second adhesive is applied to an area of a panel 910 corresponding to the edge of the joint. In step 2440, a release liner is laminated to the second adhesive.

In step 2450, the adhesive-edge building panels produced in steps 2430 and 2440 are installed as described above. In step 2460, caulk is optionally applied between any gaps between the panels. In step 2470, the release liners are removed from the panels and the joint tape, and the joint tape is applied to the joint. Preferably, the joint tape is centered over the joint.

Method 11

Figure 25:
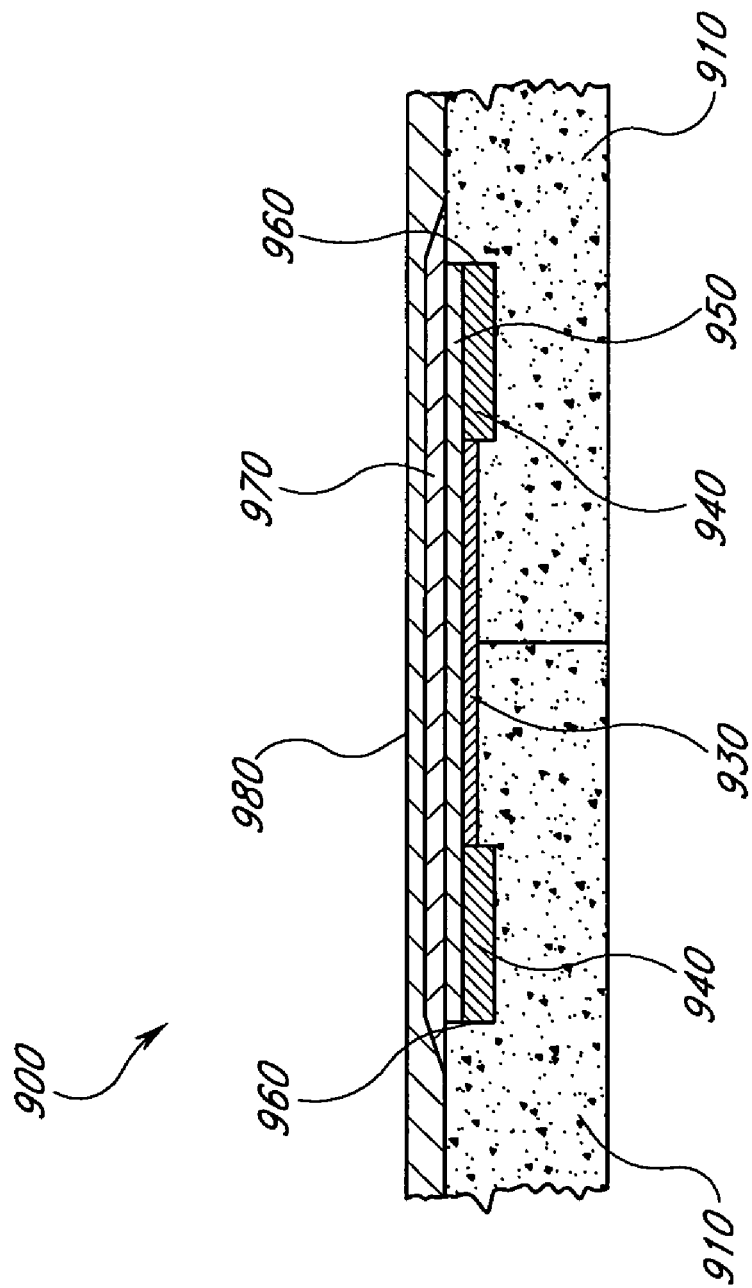
FIG. 25 is a cross section of an elastomeric joint made according to METHOD 11.

An elastomeric joint fabricated according to METHOD 11 is illustrated in FIG. 25. Elastomeric joint 900 includes two building panels 910, a flexible first adhesive layer 930, rigid second adhesive layers 940, a backing material 950, and a joint filler 970. The panels and elastomeric joint are optionally finished with a texture coating 980. The panels 910 illustrated in FIG. 25 have embossed edges and trough edges 960; however, flat panels as well as panels with only embossed edges may also be used in this method. In METHOD 11, an elastomeric joint constructed according to any of METHOD 1 through METHOD 10 is covered with a joint filler 970. In the embodiment illustrated in FIG. 25, substantially no gap is provided between the panels 910, and accordingly, no caulk is used.

Figure 26:
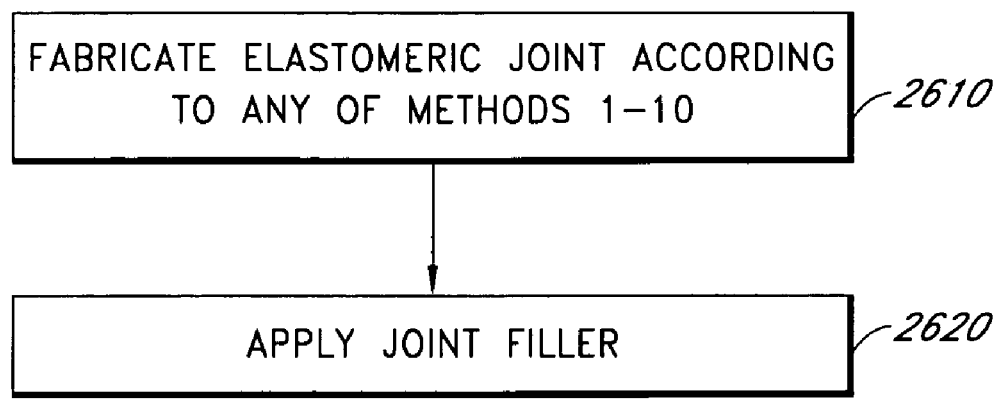
FIG. 26 is a flowchart illustrating METHOD 11 for making an elastomeric joint.

FIG. 26 illustrates METHOD 11 of constructing an elastomeric joint. In step 2610, an elastomeric joint is fabricated at the joint between adjacent building panels according to any of METHOD 1 through METHOD 10. In step 2620, a layer of joint filler 970 is applied to cover the backing material 950. In a preferred embodiment, the joint filler 970 is a ceramic putty.

The joint filler 970 simplifies the production of a panelized wall with a monolithic appearance. The joint filler provides another component in the elastomeric joint system for distributing the relative movements of adjacent panels. As is well known in the are, the joint filler may be used to cover the edges of the backing material as well as to fill any depressions in the joint or trough areas, providing a smooth surface for subsequently applied texture coatings. The joint filler may be tooled during application or may be sanded after curing to provide a smooth surface. As illustrated in FIG. 25, METHOD 11 is a preferred method when used in conjunction with trough-edge panels. Moreover, METHOD 11 is advantageously applied to wall systems constructed from panels with embossed edges or other edge profiling because the depth of the embossing need not closely match the total thickness of the backing material and adhesive. Also the width of the embossing need not closely match the width of the backing material, especially important because the panels may be installed either without gaps or with gaps of varying width. METHOD 11 is also advantageously be used with flat-edge or plain-edge panels.

In a preferred embodiment of METHOD 11, a second joint filler, preferably an elastomeric joint filler, is applied over the first joint filler, as described above.

Figure 27:
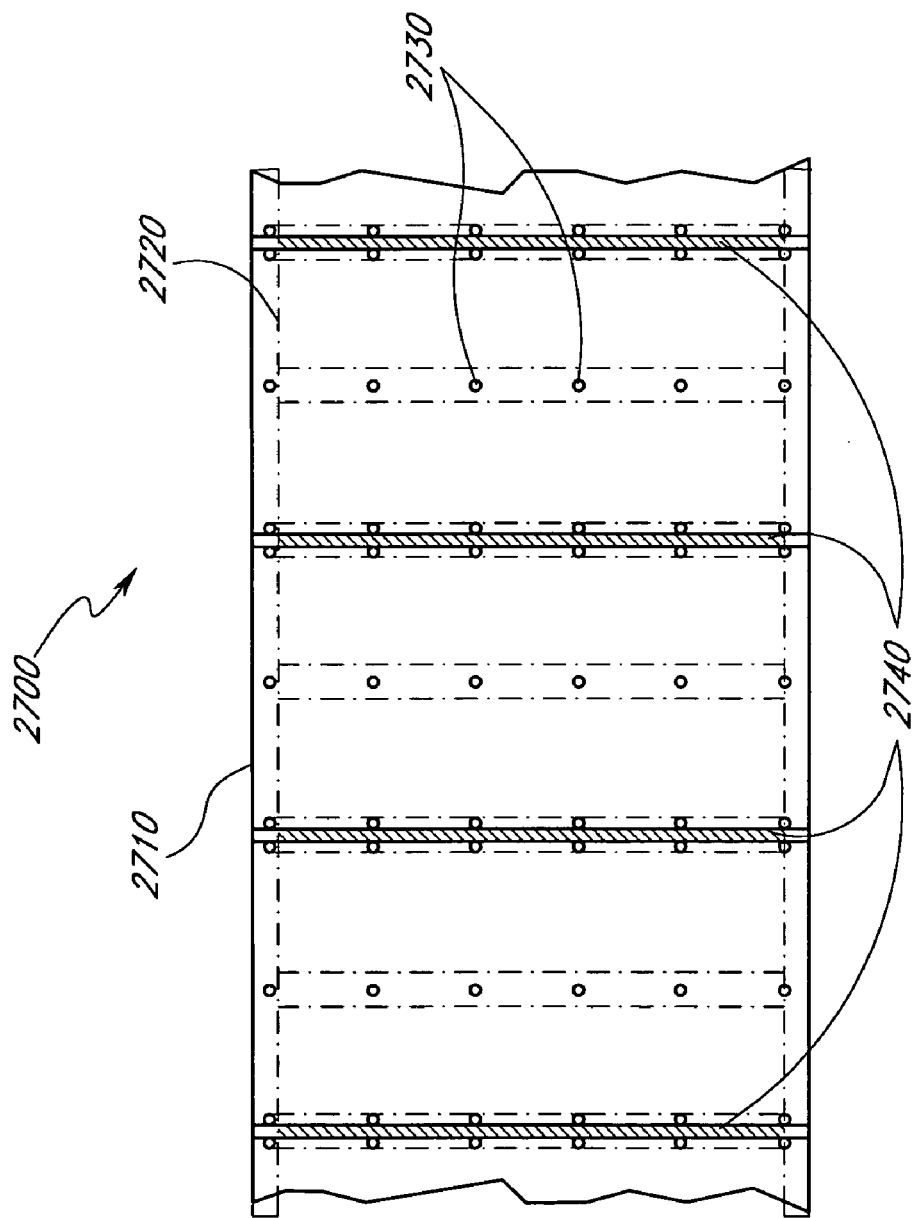
FIG. 27 is an elevation of a panelized wall system with elastomeric joints.

FIG. 27 is an elevation view of a panelized wall system 2700 composed of a frame 2710, building panels 2720, elastomeric joints 2730, and fasteners 2740.

Figure 28:
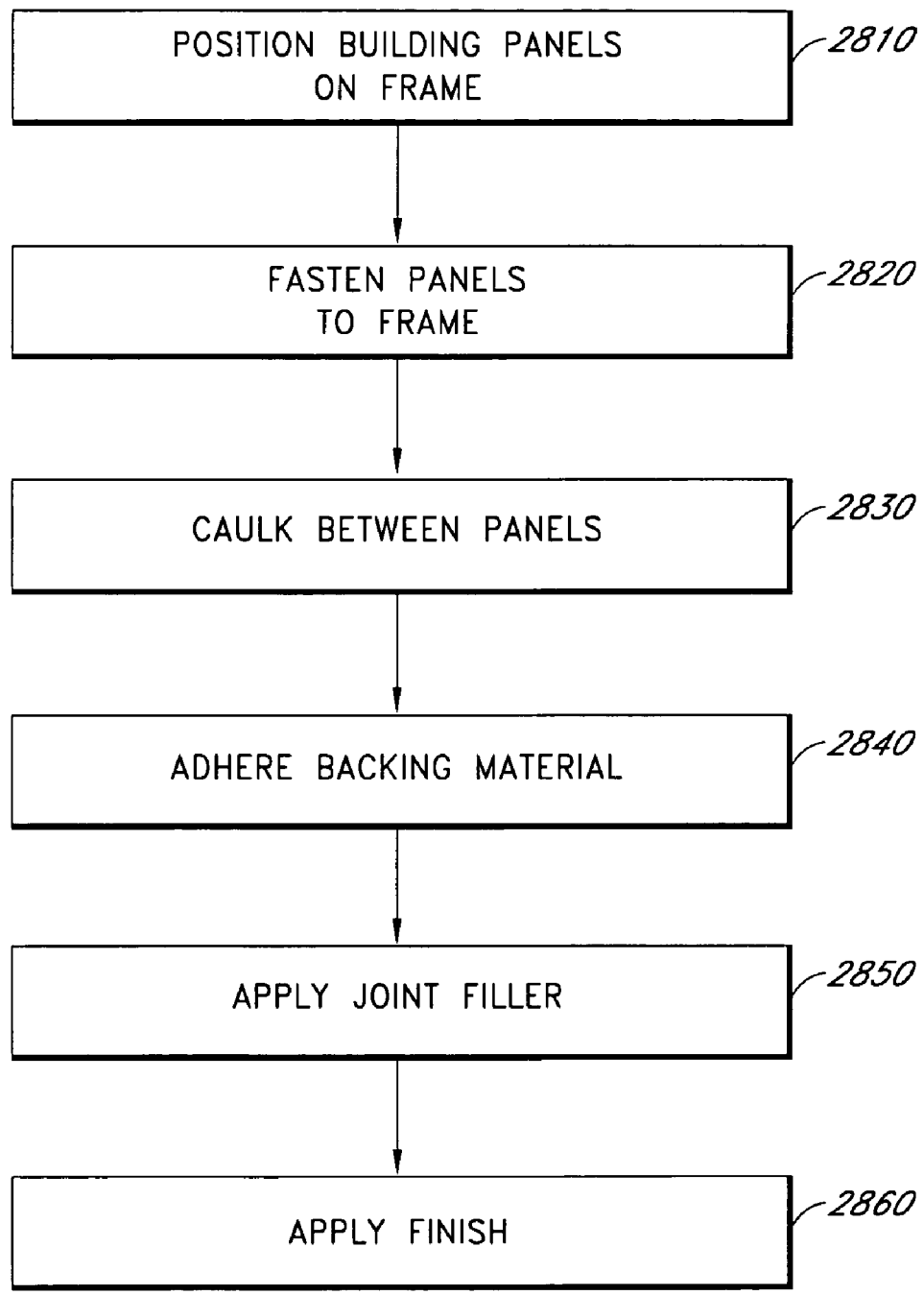
FIG. 28 is a flowchart illustrating a method of fabricating a panelized wall system with elastomeric joints.

FIG. 28 illustrates the construction of a panelized wall system according to METHOD 11. In step 2810, the back surfaces of building panels 2720 are positioned over a frame 2710 as described above. The building panels are preferably fiber cement, and may be flat, have trough edges, or embossed edges. The frame is optionally equipped with a moisture barrier, for example asphalt paper, a water break, or both. The panels are positioned over the optional moisture barrier and water break. The panels may be positioned with gaps between adjacent panels or butted, i.e., with no gaps between adjacent panels, ad described above.

In step 2820, the panels 2720 are attached to the frame 2710 with fasteners 2740 as described above. If gaps were left between adjacent panels in step 2810, in step 2830, caulk is optionally applied to fill the gaps. In step 2840, a backing material is adhered to the joints between the panels 2720. Steps 2810–2840 may be performed according to any of METHOD 1 to METHOD 10.

In step 2850, a joint filler is optionally applied over the backing material, as described above. In step 2860, an elastomeric finish is applied to the entire panelized wall system as described above.

EXAMPLE 18

A wall was framed with 2"×4" lumber, studs 16"-on-center. Asphalt paper and a water break (Homeslicker Rain Screen, Benjamin Obdyke, Horsham, Pa.) were installed on the frame. The back surfaces of 4'×8'×⅝" trough-edge fiber-cement panels were positioned over the frame level and plumb, with the edges of adjacent panels sharing a stud. That trough depth was 0.077", the trough-edge offset was 1½", and the trough width was ¾". The edges of the panels butted together leaving no gaps. The panels were nailed to the frame. The joints between the panels were taped with a tape made from 3"-wide Sontara 8804 fabric (DuPont) and a 0.010"-thick layer of Heartland Adhesive H400 (styrene-butadiene). The taped joints were then covered with a smooth, flat layer of a ceramic putty joint filler (Fill-n-Build, Global Coatings), which was allowed to cure for 1 to 2 hours. The joint filler was then covered with a smooth, flat layer of an elastomeric joint filler (Acracream, Global Coatings). The wall was allowed to cure for a minimum of about 24 hours.

A stucco covering was then applied to the wall. First, Colorseal Plus Primer (Global Coatings) was applied to the entire wall surface with a paint roller and allowed to dry for 1 to 2 hours. Next, Carrara texture (Global Coatings) was shot onto the wall with a hopper gun. At this point, the surface may be left "as is" for a "sanded" finished or hand-troweled to the desired finish. The stucco finish was protected until cured.

EXAMPLE 19

A panelized wall was constructed according to EXAMPLE 18 except that the frame included 4'×8'×½" OSB shear panels attached to the studs, followed by the asphalt paper and the water break.

EXAMPLE 20

The comparative performances in a racking test of a wall constructed according to the preferred method disclosed in U.S. Pat. No. 5,732,520 and a wall constructed according to the present disclosure were evaluated in this test.

The test walls were constructed in a testing device as described in ASTM E 72-(98). The walls were 8'×8' walls framed with 2"×4" lumber, studs 16"-on-center. Two fiber-cement panels with plain edges, 4'×8'×5/16" (Hardiepanel, James Hardie, Fontana, Calif.), were positioned on the frame, their adjacent edges sharing a stud with a ⅛" gap between them. The panels were attached to the frame. The gap between the panels was caulked with Chem-calk 900 (Bostik Findley), the surface of the caulk smoothed, and the caulk allowed to cure overnight. The joints were then taped with either the joint tape of U.S. Pat. No. 5,732,520 or a joint tape according to the present disclosure. The joints were finished with a smooth stucco coating (Multitex, Multicoat, Costa Mesa, Calif.). Finally, both walls and joints were finished with a medium texture stucco coating (Multitex, Multicoat, Costa Mesa, Calif.).

The joint tape of U.S. Pat. No. 5,732,520 is a commercially available 3"-wide wide self-adhesive joint tape (Multicoat, Costa Mesa, Calif.) made from a fabric backing and a pressure sensitive adhesive. The joint tape of the present disclosure is a 3"-wide self-adhesive joint tape made from Sontara 8004 fabric and a 0.010"-thick layer of Heartland Adhesive H400 (styrene-butadiene).

Figure 29:
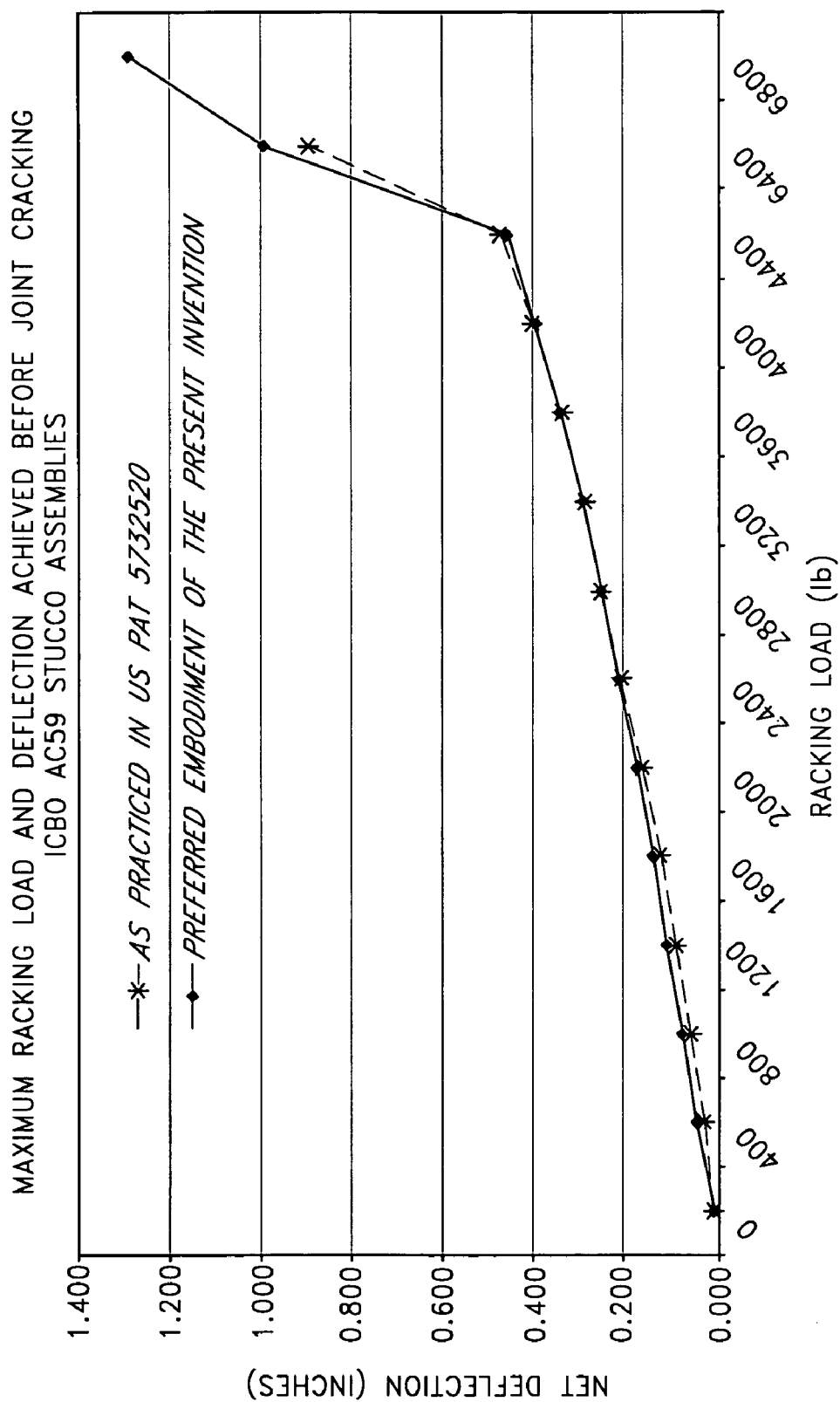
FIG. 29 illustrates the comparative performances of a wall constructed according to U.S. Pat. No. 5,732,520 and a wall constructed according to the present disclosure in a racking test.

Each wall was subjected to a racking load according to the test method. The results are provided in FIG. 29. The wall constructed according to the disclosed method withstood a higher racking load and deflection before cracking at the panel joints.

The embodiments illustrated and described above are provided as examples of certain preferred embodiments of the present invention. Various changes and modifications can be made to the embodiments presented herein by those skilled in the art without departure from the spirit and scope of this invention, the scope of which is limited only by the claims appended hereto.

What is claimed is:

1. A method of constructing a caulkless panelized wall system, comprising:
    positioning at least two building panels over a frame, wherein
        the at least two building panels are substantially cementitious,
        each panel comprises a front surface, a back surface, and a plurality of edges,
        the back surfaces of the panels are positioned over the frame,
        the two panels are positioned adjacent to each other, forming a seam between the adjacent panels, and
        the two panels are substantially coplanar;
    fastening the panels to the frame; and
    forming a caulkless elastomeric joint comprising a backing material adhered over the seam, wherein the backing material is adhered to the front surfaces of the adjacent panels without any caulk applied to the seam between the adjacent panels.

2. The method of claim 1, wherein the panels are fiber cement.

3. The method of claim 1, wherein the adjacent panels are positioned with no gap therebetween.

4. The method of claim 1, wherein the adjacent panels are positioned with a gap therebetween.

5. The method of claim 4, wherein the gap is about ⅛" wide.

6. The method of claim 1, wherein the backing material is a fabric.

7. The method of claim 6, wherein the backing material is from about 0.0005" to about 0.04" thick.

8. The method of claim 6, wherein the fabric is a non-woven polyester fabric.

9. The method of claim 6, wherein the fabric is a polyamide mesh.

10. The method of claim 1, wherein the backing material is about 3" wide.

11. The method of claim 1, wherein the backing material is applied as a joint tape, wherein the joint tape comprises an adhesive preapplied to a face of the backing material.

12. The method of claim 1, wherein the caulkless elastomeric joint further comprises a ceramic putty applied over the backing material.

13. The method of claim 12, wherein the caulkless elastomeric joint further comprises an elastomeric joint filler applied over the ceramic putty.

14. The method of claim 1 further comprising applying an elastomeric finish to the panelized wall system.

15. The method of claim 14, wherein the elastomeric finish comprises an elastomeric primer and an elastomeric texture layer.

16. The method of claim 14, wherein the elastomeric finish is a texture coating.

17. The method of claim 1, wherein the frame is a wood frame.

18. The method of claim 1, wherein the frame comprises shear panels.

19. The method of claim 1, wherein the frame comprises a moisture barrier.

20. The method of claim 1, wherein the frame comprises a water break.

21. A caulkless panelized wall system comprising
    a frame;
    at least two building panels positioned over the frame, wherein
        the at least two building panels are substantially cementitious;
        each panel comprises a front surface, a back surface, and a plurality of edges,
        the back surfaces of the panels are positioned over the frame,
        the two panels are positioned adjacent to each other, forming a seam between the adjacent panels with no caulk applied to the seam,
        the panels are fastened to the frame, and
        no caulk is applied to the seam; and
    a caulkless elastomeric joint comprising a backing material adhered over the seam between the adjacent panels, wherein the backing material is adhered to the front surfaces of the adjacent panels without any caulk applied to the seam between the adjacent panels.

22. The caulkless panelized wall system of claim 21, wherein the panels are fiber cement.

23. The caulkless panelized wall system of claim 21, wherein the adjacent panels are positioned with no gap therebetween.

24. The caulkless panelized wall system of claim 21, wherein the adjacent panels are positioned with a gap therebetween.

25. The caulkless panelized wall system of claim 24, wherein the gap is about ⅛" wide.

26. The caulkless panelized wall system of claim 21, wherein the backing material is a fabric.

27. The caulkless panelized wall system of claim 26, wherein the backing material is from about 0.0005" to about 0.04" thick.

28. The caulkless panelized wall system of claim 26, wherein the fabric is a non-woven polyester fabric.

29. The caulkless panelized wall system of claim 26, wherein the fabric is a polymamide mesh.

30. The caulkless panelized wall system of claim 21, wherein the backing material is about 3" wide.

31. The caulkless panelized wall system of claim 21, wherein the backing material is applied as a joint tape, wherein the joint tape comprises an adhesive preapplied to a face of the backing material.

32. The caulkless panelized wall system of claim 21, wherein the caulkless elastomeric joint further comprises a ceramic putty applied over the backing material.

33. The caulkless panelized wall system of claim 32, wherein the caulkless elastomeric joint further an elastomeric joint filler applied over the ceramic putty.

34. The caulkless panelized wall system of claim 21 further comprising applying an elastomeric finish to the panelized wall system.

35. The caulkless panelized wall system of claim 34, wherein the elastomeric finish comprises an elastomeric primer and an elastomeric texture layer.

36. The caulkless panelized wall system of claim 34, wherein the elastomeric finish is a texture coating.

37. The caulkless panelized wall system of claim 21, wherein the frame is a wood frame.

38. The caulkless panelized wall system of claim 21, wherein the frame comprises shear panels.

39. The caulkless panelized wall system of claim 21, wherein the frame comprises a moisture barrier.

40. The caulkless panelized wall system of claim 21, wherein the frame comprises a water break.

* * * * *